(12) United States Patent
Marcus

(10) Patent No.: US 11,877,960 B2
(45) Date of Patent: Jan. 23, 2024

(54) EXTREMITY OFFLOADING SYSTEM

(71) Applicant: Michael J. Marcus, Corona Del Mar, CA (US)

(72) Inventor: Michael J. Marcus, Corona Del Mar, CA (US)

(*) Notice: Subject to any disclaimer, the term of this patent is extended or adjusted under 35 U.S.C. 154(b) by 1 day.

(21) Appl. No.: 17/455,342

(22) Filed: Nov. 17, 2021

(65) Prior Publication Data

US 2022/0160568 A1 May 26, 2022

Related U.S. Application Data

(60) Provisional application No. 63/116,652, filed on Nov. 20, 2020.

(51) Int. Cl.
*A61G 13/00* (2006.01)
*A61G 13/12* (2006.01)
*A61G 7/075* (2006.01)

(52) U.S. Cl.
CPC ....... *A61G 13/1245* (2013.01); *A61G 7/0755* (2013.01)

(58) Field of Classification Search
CPC .. A61F 5/042; A61F 5/05; A61F 5/058; A61F 5/05841; A61F 5/0585; A61F 5/37; A61F 5/3761; A61F 5/3769; A61G 7/065; A61G 7/075; A61G 7/1082; A61G 7/1092; A61G 7/1094; A61G 13/12; A61G 13/124; A61G 13/122; A61G 13/1235; A61G 13/1245
USPC ........................................................ 128/845
See application file for complete search history.

(56) References Cited

U.S. PATENT DOCUMENTS

| | | | |
|---|---|---|---|
| 814,795 A * | 3/1906 | Myers | A61F 13/04 602/6 |
| 3,345,656 A | 10/1967 | Steinman | |
| 3,901,228 A | 8/1975 | Brown | |
| 3,939,829 A | 2/1976 | Spann | |
| 3,946,451 A | 3/1976 | Spann | |
| 4,104,746 A * | 8/1978 | Goetz | A61F 13/069 5/922 |
| 4,186,738 A | 2/1980 | Schleicher et al. | |
| 4,573,456 A * | 3/1986 | Spann | A61F 13/069 602/6 |

(Continued)

FOREIGN PATENT DOCUMENTS

| | | |
|---|---|---|
| GB | 6206707 | 5/2022 |
| JP | 2015-198681 A | 11/2015 |

(Continued)

OTHER PUBLICATIONS

International Search Report issued for International Patent Application No. PCT/US2021/072459, dated Feb. 10, 2022 in 5 pages.

(Continued)

*Primary Examiner* — Adam Baker
(74) *Attorney, Agent, or Firm* — Knobbe, Martens, Olson & Bear, LLP

(57) ABSTRACT

A extremity offloading system including a body with an outer surface, an inner surface, and a first thickness extending between the outer surface and the inner surface. The outer surface can be at least partially round. The inner surface can define an aperture. The aperture can be configured to accept insertion of a leg or an ankle of a patient.

20 Claims, 35 Drawing Sheets

(56) References Cited

U.S. PATENT DOCUMENTS

| | | | |
|---|---|---|---|
| 4,616,639 A | 10/1986 | Huber | |
| D287,641 S | 1/1987 | Schaefer | |
| 4,926,884 A | 5/1990 | Lonardo | |
| 5,725,486 A | 3/1998 | Engelman | |
| 5,745,939 A | 5/1998 | Flick et al. | |
| 5,839,139 A | 11/1998 | Fink | |
| 5,957,874 A | 9/1999 | Klein | |
| 6,186,967 B1 * | 2/2001 | Messina | A61F 5/01 128/882 |
| D469,541 S | 1/2003 | Cheatham | |
| D482,791 S | 11/2003 | Moses | |
| 6,846,295 B1 | 1/2005 | Ben-Nun | |
| 7,188,382 B1 | 3/2007 | Taylor et al. | |
| D582,045 S | 12/2008 | James | |
| 7,584,755 B2 * | 9/2009 | Reid | A61F 5/05858 602/5 |
| 8,479,333 B2 | 7/2013 | Gould et al. | |
| D719,662 S | 12/2014 | Pope | |
| 9,119,760 B2 | 9/2015 | Purdy et al. | |
| D749,209 S | 2/2016 | Uhlenkamp et al. | |
| 9,301,868 B2 | 4/2016 | Castle | |
| D777,935 S | 1/2017 | Shaffer | |
| D787,078 S | 5/2017 | Daniels | |
| 9,648,959 B2 | 5/2017 | Frydman | |
| 10,016,326 B2 | 7/2018 | Purdy et al. | |
| D886,495 S | 6/2020 | Wong | |
| D897,730 S | 10/2020 | Chan | |
| D897,731 S | 10/2020 | Chan | |
| D901,943 S | 11/2020 | Abraham | |
| D940,338 S | 1/2022 | Alexandrescu et al. | |
| D940,961 S | 1/2022 | Heath | |
| D955,066 S | 6/2022 | Miller | |
| D979,777 S | 2/2023 | Mao | |
| D982,934 S | 4/2023 | Afshar et al. | |
| 2012/0253250 A1 | 10/2012 | Spahn et al. | |
| 2014/0194796 A1 | 7/2014 | Noskowicz et al. | |
| 2016/0113408 A1 | 4/2016 | Shaffer | |
| 2016/0296030 A1 | 10/2016 | Frydman | |
| 2018/0028345 A1 * | 2/2018 | Karasahin | B23P 11/00 |
| 2019/0167506 A1 | 6/2019 | Sung | |

FOREIGN PATENT DOCUMENTS

| | | | |
|---|---|---|---|
| KR | 10-1920366 B1 | 11/2018 | |
| WO | WO 2009/147316 A2 | 12/2009 | |
| WO | WO 2022/256649 A1 | 12/2022 | |

OTHER PUBLICATIONS

Written Opinion issued for International Patent Application No. PCT/US2021/072459, dated Feb. 10, 2022 in 4 pages.

Saf Heel Protector, https://web.archive.org/web/20200813081641/ https://www.astrislifecare.com.au/product/saf-heel-protector/; dated as being available on Aug. 13, 2020.

DOITOOL foot Elevation Pillows Ankle Heel Elevator Wedge Foot Support, DOITOOL, Amazon.com, [Dated: Mar. 22, 2021], [Site accessed: Sep. 26, 2023], seen at URL: http://www.amazon.com/ DOITOOL-Elevation-Elevator-Pressure-Sleeing/dp/B08ZMMGJ1Y/ ref=sr_1_17 (Year: 2021).

Heel Boot Protector | Heel Protecting Foam Positioner with Adjustable straps, American Hospital Supply Ahs, Amazon.com, [Post date: Feb. 28, 2023], [Site accessed: Sep. 26, 2023], seen at URL: https://www.amazon.com/dp/B0BX4QG4CJ/ref=sspa_dk_detail_7 (Year: 2023).

* cited by examiner

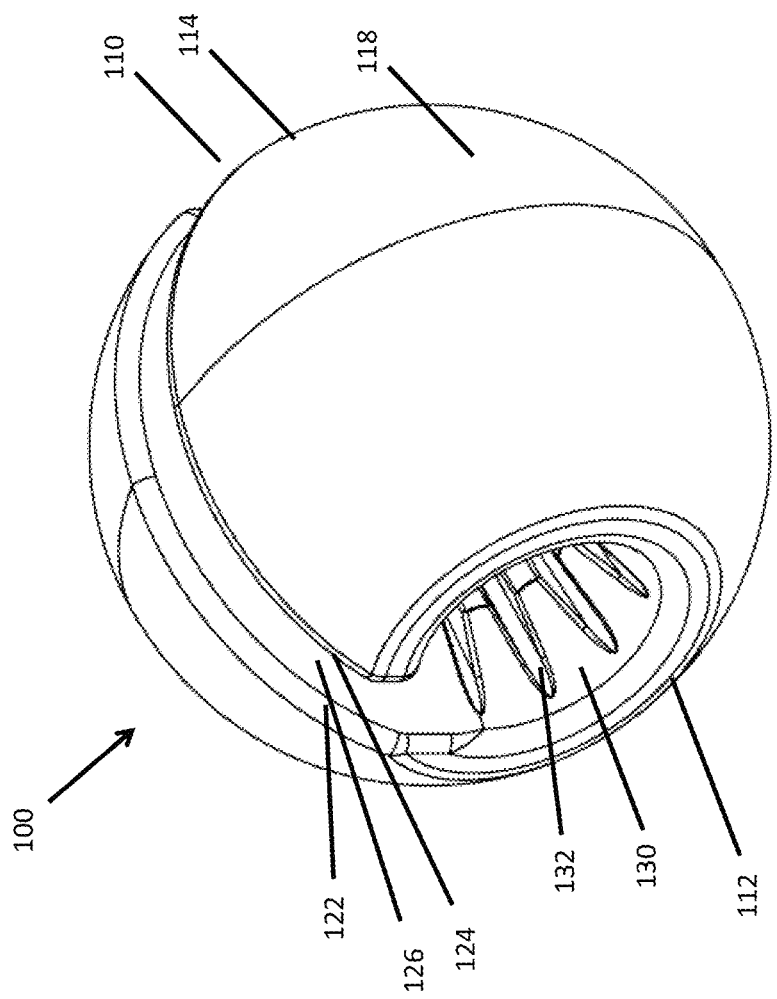

EXTREMITY OFFLOADING SYSTEM

CROSS-REFERENCE TO RELATED APPLICATION(S)

This application claims the benefit of U.S. Provisional Application No. 63/116,652, filed Nov. 20, 2020, which is hereby incorporated by reference in its entirety. Any and all applications, if any, for which a foreign or domestic priority claim is identified in the Application Data Sheet of the present application are hereby incorporated by reference in their entireties under 37 CFR 1.57.

BACKGROUND

Various extremity offloading systems have been used in the healthcare industry to try and prevent a deep tissue pressure injury (DTPI), such as decubitus ulcers or bedsores, in patients who are on bed rest or generally immobile, but with limited success. The risk for a DTPI can develop anywhere on the body and, in particular, at any bony prominence of the body, such as the foot or ankle. In some cases, patients can have low or no sensitivity in areas in their body, such that the patient can be unaware DTPIs may be developing, which can lead to further complications. Initially, the area of the body develops a redness, which if left to progress can develop into a blister. This blister can subsequently become infected, which can then become an ulceration or DTPI. Not only can the development of a DTPI be painful, but they more importantly may also cause further complications, such as infections, osteomyelitis, sepsis, limb loss, or possibly even death. These further complications for patients can often lead to protracted and expensive extended hospital stays. Thus, preventing hospital acquired pressure injuries (HAPIs) is prudent for both health and financial reasons. These HAPIs may range in severity depending upon the depth of the tissue damage. They also vary in location, such as a heel, which is a commonly affected region. Treatment protocols may range from the use of topical antibiotics creams, oral antibiotics, IV medications, enzymatic debridement ointments. Further treatment may involve surgical debridement, grafting and use of vacuum assisted devices to heal the affected tissues. With severe tissue damage extending to the bone, surgical intervention may be required for limb salvage. These interventions can include ulceration excision, bone resection and skin flap closures. Some complicated cases may require prolonged hospitalizations with possible referral to skilled nursing facilities.

SUMMARY

The systems, methods and devices of this disclosure each have several innovative aspects, no single one of which is solely responsible for the desirable attributes disclosed herein.

In one aspect, an extremity offloading system can include a body with an outer surface, an inner surface, and a thickness extending between the outer surface and the inner surface. The outer surface can be at least partially round. The inner surface can define an aperture. The aperture can be configured to accept insertion of a leg or an ankle of a patient.

In some examples, the body can include a proximal end and a distal end, wherein the aperture extends through the proximal end and the distal. The proximal end and the distal end can each be flat. The aperture can be cylindrical. A diameter of the aperture at the proximal end and a diameter of the aperture at the distal end can each be greater than a diameter of the aperture at the middle of the body.

In some aspects, the inner surface can include a plurality of flutes. A length of each of the plurality of flutes can extend along a length of the aperture. Each of the plurality of flutes can be equally spaced about a circumference of the aperture. The plurality of flutes can include 10 flutes. The inner surface can include a plurality of portions between each of the plurality of flutes. Each of the plurality of portions can include a flat surface. Each flat surface can be configured to be in contact with the leg or the ankle of the patient. Corners between each of the plurality of flutes and each of the plurality of portions can be rounded.

In some examples, the body includes an opening extending through a side of the body. The opening can extend through a thickness of the body between the outer surface and the inner surface. The opening can be angled relative to a longitudinal axis of the body. The longitudinal axis can extend from a proximal end to a distal end of the body. The opening can be defined by a first edge and a second edge of the body. The first edge and the second edge can be parallel. The first edge and the second edge can each be beveled.

In some aspects, the extremity offloading system can include one or more sensors configured to measure one or more of movement, pressure, temperature, humidity, or at least one patient parameter. The one or more sensors can include at least an accelerometer, a gyroscope, and a temperature sensor. The body can include foam.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting on scope.

FIG. 9 illustrates a perspective view of another embodiment of a extremity offloading system.

DETAILED DESCRIPTION

Figure 1:
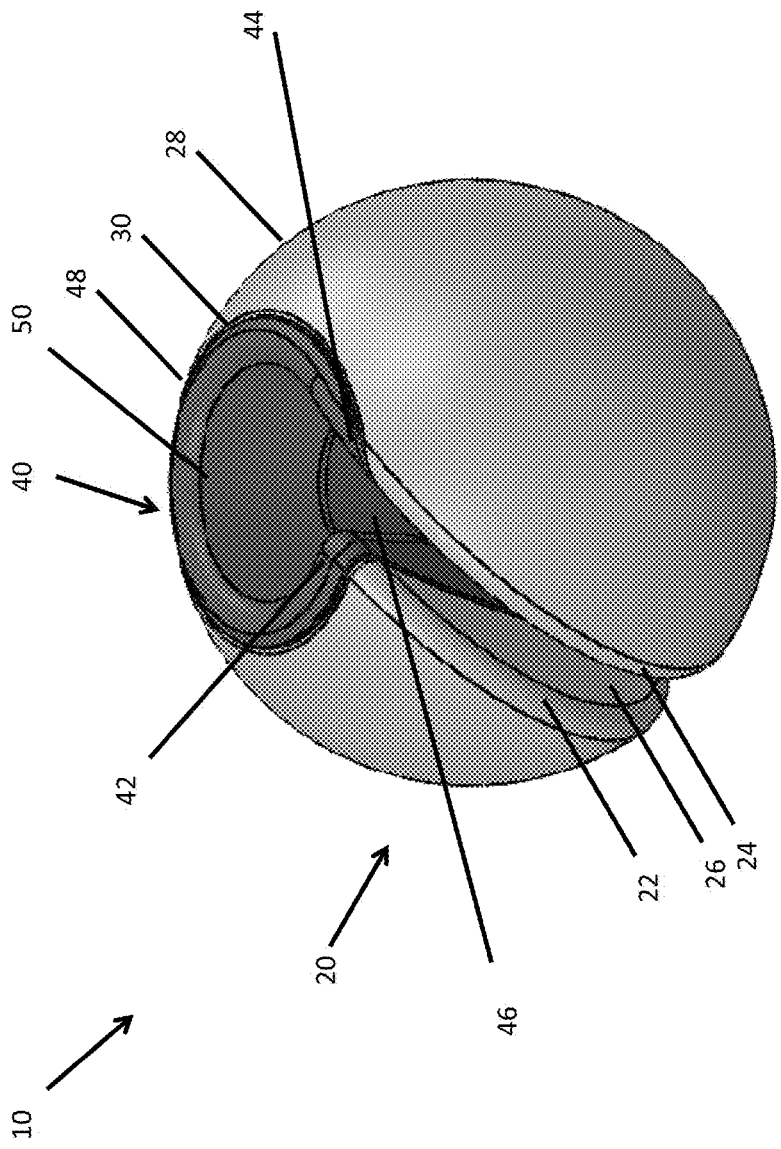
FIG. 1 illustrates a proximal perspective view of an extremity offloading system.
Figure 2:
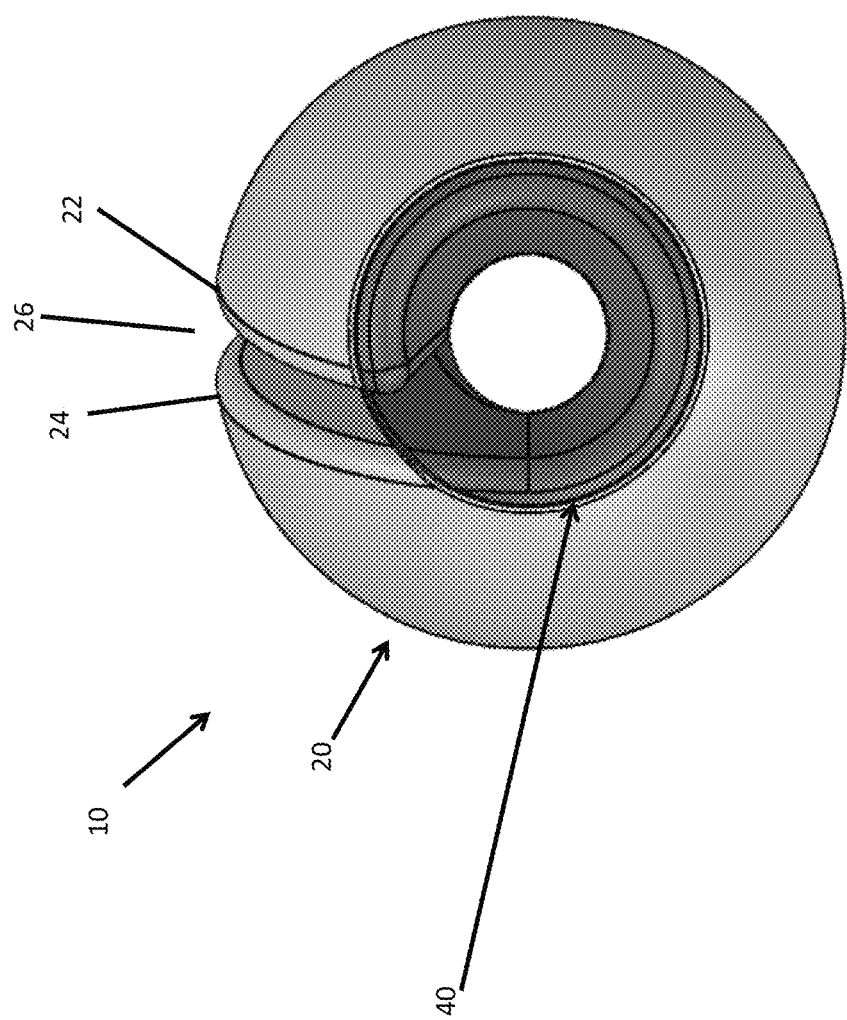
FIG. 2 illustrates an axial view of the extremity offloading system of FIG. 1.

Offloading can be an effective and efficient method of preventing DPTIs, whether in home environments or clinical settings. This unfortunate complication can affect a large variety of patients that are being treated for a myriad of reasons. Prevention of this type of injury not only improves patient outcomes, but also reducing excess medical costs. Once DTPIs develop, efficient methods of offloading can also be important for proper healing. In more severe cases, which can require extensive surgical interventions for tissue injuries to the heel, foot, or ankle, offloading can also be mandatory. All kinds of patients, but especially those with compromised blood flow, can be particularly at risk for DTPI. In the current healthcare climate, the most common patient population being affected includes diabetics, patients with peripheral arterial disease, stroke patients, and any patient who requires prolonged immobilization. Often these patients suffer from neuropathic problems that prevent them from feeling or perceiving the injury. Furthermore, complications due to COVID-19 can further contribute to the risk and development of DTPIs.

There are various solutions used to offload pressure on extremities to prevent DTPI or to allow patients to heal post recovery from surgical intervention and especially to keep pressure or weight off the back of a patient's heel. For example, a pillow or cushion can be positioned underneath a patient's leg or ankle when the patient's leg is substantially horizontal to a surface (e.g. when a patient is laying or sitting in bed). The pillow or cushion can elevate the patient's foot and keep pressure or weight off the back of the patient's heel. However, it can be difficult to achieve the desired position of the pillow and the patient's leg. Moreover, the desired position can be difficult to maintain. Patient compliance can also be difficult to achieve when a pillow or cushion is used. For example, since there is nothing to secure the pillow or cushion to the patient, the patient can shift or move out of the desired position, thereby reducing the effectiveness of the procedure and possibly even causing further injury.

Some systems seek to address these problems by using hoops, casts, braces, or devices that strap to the leg of a patient. However, these devices can be complicated to apply to a patient, in particular if the device has numerous straps and/or multiple holes for straps. These devices can also require frequent monitoring or adjustment, which can require attention from a medical professional. Furthermore, the use of straps or other means to secure a device to a patient can, by themselves, cause injury to the patient, in particular if the straps are incorrectly used or applied. For example, the straps can be in the wrong position or may be too loose or too tight.

Further, these devices may not allow a patient any type of movement or if a patient moves that can diminish the effectiveness of the device. For example, a heel suspension hoop can hold a patient's leg in the proper position but if the patient needs to be moved or if a patient moves, the patient's leg must be removed from the heel suspension hoop. In other examples, a leg cast or brace can be used to keep pressure off the back of a heel, but such devices can be cumbersome or complicated to apply and maintain. In some cases, the devices can be difficult to remove or attach (which may have to be done numerous times to allow for inspections or further procedures to the affected area). Patients may attempt to move or walk with the cast or brace on, which can lead to accidents or falls. Furthermore, if the patient moves with those devices the device position may change, which reduces the effectiveness and can even promote further injury. For example, the device can cause at least one leg of the patient to be positioned at an angle to elevate the heel, which can lead to issues in other parts of the patient's body (such as undesired pressure in another portion of the body). Furthermore, these types of devices can be expensive and difficult to store.

As shown in FIGS. 1-7, the extremity offloading system 10 includes a first component or portion 20 and a second component or portion 40. The extremity offloading system 10 can also be called a support system, a support assembly, a suspension system, a suspension assembly or a sphere for an extremity, limb, or heel. The first component 20 can be an outer component that is configured to receive or engage with the second component 40. Although described as being formed from two components 20 and 40, it should be understood that the extremity offloading system 10 can be formed from a single component (e.g., a unibody device) or formed from more than two components. The first component 20 can have an outer surface 28 that is spherical or round or at least partially spherical or round. As shown, the proximal end and the distal end can each be flat, such that the first component 20 does not form a full sphere. The proximal end can be considered the top end. The distal end can be considered the bottom end. Furthermore, in some embodiments, the proximal end and distal end may be reversed. The first component 20 can have a first thickness between the inner surface 30 and the outer surface 28.

Figure 3:
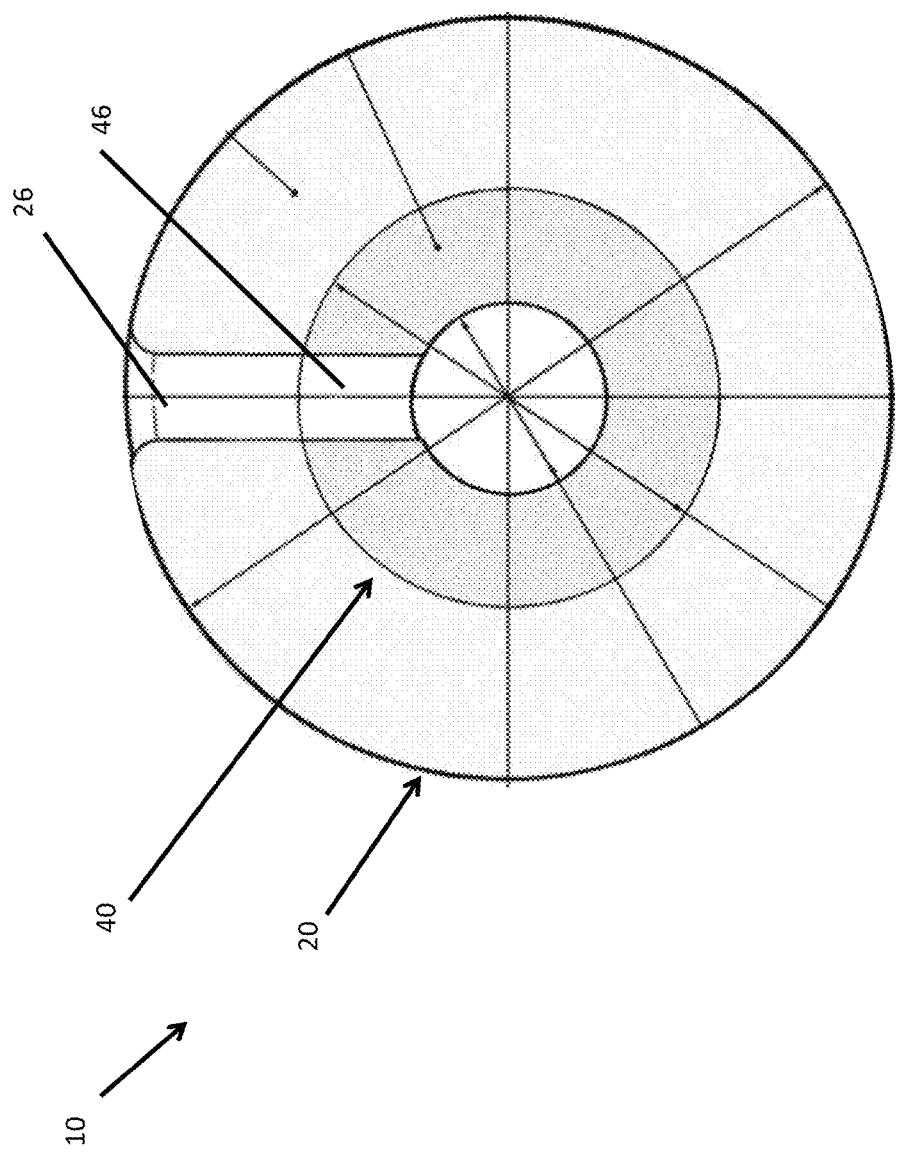
FIG. 3 illustrates a cross-sectional proximal view along the width of the extremity offloading system of FIGS. 1-2.
Figure 4:
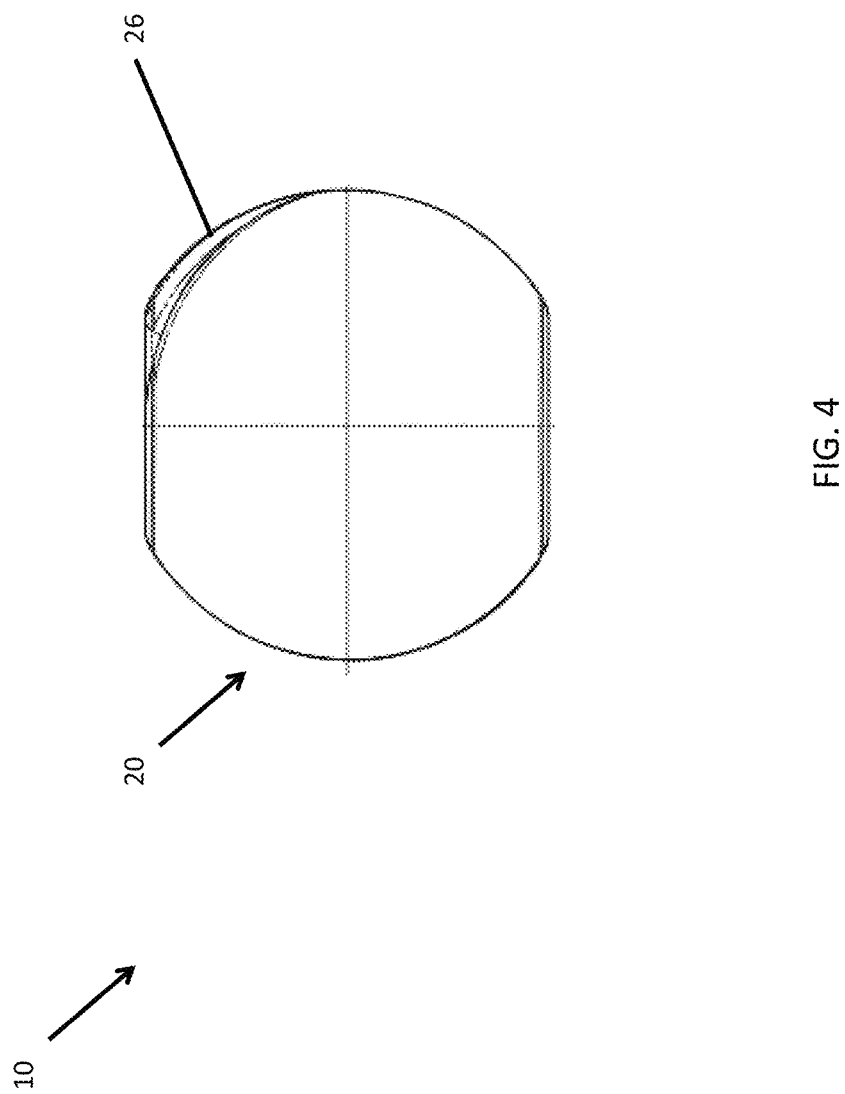
FIG. 4 illustrates a medial view of the extremity offloading system of FIGS. 1-3.
Figure 6:
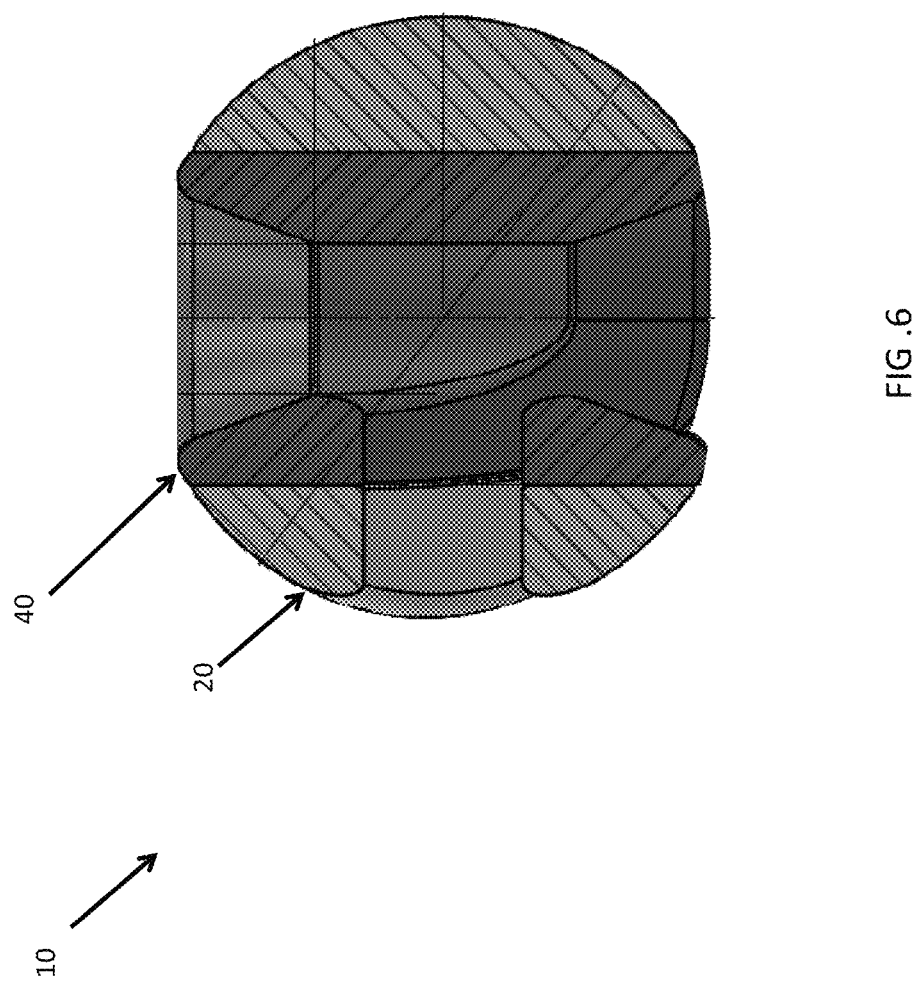
FIG. 6 illustrates a cross-sectional medial view along the length of the extremity offloading system at line A-A of FIG. 5.
Figure 7:
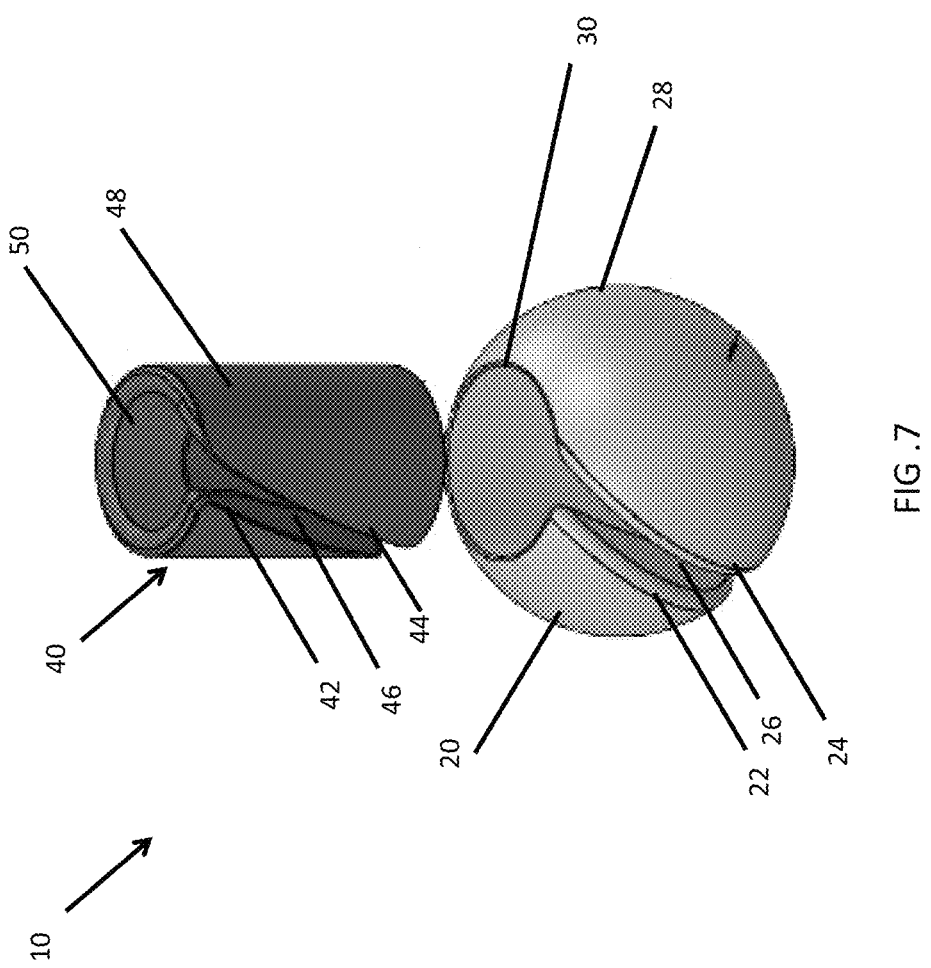
FIG. 7 illustrates an exploded view of the extremity offloading system of FIGS. 1-6.

The first component 20 can also have a central or first aperture that is defined by the inner surface 30. The inner surface 30 can be cylindrical or at least partially cylindrical. In some examples, the central aperture defined by the inner surface 30 is a cylindrical or partially cylindrical aperture. As shown in FIG. 3, which illustrates a cross-sectional view along the width of the extremity offloading system 10, the central aperture can be a circle. In other examples, the central aperture can have different shapes, such as square, rectangular, triangular or another rounded shape (e.g. oval), in the cross sectional view along the width of the extremity offloading system 10. The central aperture can extend from the first end to the second end along the length of the first component 20. As shown in FIG. 6, which illustrates a cross-sectional view along the length of the extremity offloading system 10, the central aperture of the first component 20 can be rectangular in the cross sectional view. The diameter of the central aperture can be constant along the length of the first component 20. The central aperture defined by the inner surface 30 can receive the second component 40.

In some examples, the length between the first end and the second end of the first component 20 can be between 5 to 10 inches, such as between 5 to 6 inches, 6 to 7 inches, 7 to 8 inches, 8 to 9 inches, or 9 to 10 inches. In some examples, the outer diameter or width of the first component 20 can be between 5 to 15 inches, such as between 5 to 7 inches, 7 to 9 inches, 9 to 11 inches, 11 to 13 inches, or 13 to 15 inches. In some examples, the diameter of the central aperture of the first component 20 can be between 5 to 10 inches, such as between 5 to 6 inches, 6 to 7 inches, 7 to 8 inches, 8 to 9 inches, or 9 to 10 inches. It should be understood that the dimensions are not limited as such and the lengths and/or diameters may be lesser or greater than the disclosed examples.

The second component 40 can be an inner component that is configured to be within the first component 20. For example, the second component 40 can be received within the central aperture defined by the inner surface 30 of the first component 20. In some examples, the first component 20 and the second component 40 can be separate components, which can advantageously allow adjustment or replacement of individual components. In some examples, the first component 20 and the second component 40 can be bonded together. In some examples, the first component 20 and the second component 40 can be integral, which can allow for ease of use and transportation.

The second component 40 can be configured to receive at least a portion of a patient's leg, such as a patient's ankle or lower leg. The second component 40 can have an outer surface 48 that is cylindrical or at least partially cylindrical. The second component 40 can have a second thickness between the inner surface 50 and the outer surface 48.

The second component 40 can have an inner surface 50 that is cylindrical or at least partially cylindrical. The inner surface 50 can be configured to wrap around or partially wrap around a portion of a patient's leg or ankle. The inner surface 50 can define a central aperture configured to receive a portion of a patient's leg or ankle.

In some examples, the central aperture defined by the inner surface 50 is a cylindrical or partially cylindrical aperture. As shown in FIG. 3, which illustrates a cross-sectional view along the width of the extremity offloading system 10, the central aperture of the second component 40 can be a circle. In other examples, the central aperture can have different shapes, such as a partially rounded shape or an oval shape, in the cross sectional view along the width of the extremity offloading system 10. The central aperture can extend from the first end to the second end along the length of the second component 40. As shown in FIG. 6, which illustrates a cross-sectional view along the length of the extremity offloading system 10, a portion of the central aperture of the second component 40 can be rectangular in the cross sectional view. The first end and the second end of the central aperture of the second component 40 can be angled, such that the diameter increase towards the first end and the second end of the second component 40. As shown in FIG. 6, the cross-sectional view of the first end and second end of the central aperture of the second component 40 can be sloped or triangular in the cross-sectional view. For example, in some examples, the diameter of the central aperture of the second component 40 can be a first diameter in the center of the second component. The diameter of the central aperture towards the first end and the second end can be a second diameter, the second diameter greater than the first diameter. The diameter of the central aperture can gradually increase from the first diameter at the center to the second diameter at the first end or at the second end, such that the inner surface 50 can be sloped as the diameter increases.

In some examples, the length between the first end and the second end of the second component 40 can be between 5 to 10 inches, such as between 5 to 6 inches, 6 to 7 inches, 7 to 8 inches, 8 to 9 inches, or 9 to 10 inches. In some examples, the diameter of the second component 40 can be between 5 to 15 inches, such as between 5 to 7 inches, 7 to 9 inches, 9 to 11 inches, 11 to 13 inches, or 13 to 15 inches. In some examples, the first diameter of the central aperture of the second component 40 can be between 1 to 5 inches, such as between 1 to 2 inches, 2 to 3 inches, 3 to 4 inches, or 4 to 5 inches. In some examples, the second diameter of the central aperture of the second component 40 can be between 5 to 10 inches, such as between 5 to 6 inches, 6 to 7 inches, 7 to 8 inches, 8 to 9 inches, or 9 to 10 inches. It should be understood that the dimensions are not limited as such and the lengths and/or diameters may be lesser or greater than the disclosed examples.

The first component 20 and the second component 40 can be constructed from any material, such as foam. In some examples, the first component 20 and the second component 40 can be made of the same material or different material. In some examples, the first component 20 can be made of a material that has an increased firmness compared to the material of the second component 40. In some examples, the second component 40 can made of memory foam. The reduced firmness of the second component 40 can be provided for the comfort of the patient and to reduce the risk of irritation, as the second component 40 can be in direct contact with the patient's leg. The increased firmness of the first component 20 can be provided to provide support to the patient's leg or ankle as the patient applies weight against the extremity offloading system 10, which may rest on a surface. In some examples, the first component 20 and/or the second component 40 can be made of an antimicrobial or antibacterial material. In some examples, the material of the first component 20 and/or the second component may include holes or may be made of a breathable material for the patient's comfort and to prevent infection. In some cases, the first component 20 and/or the second component 40 can be coated in a layer of an antimicrobial or antibacterial material. In some examples, the first component 20 and/or the second component 40 can be made of a material that is latex free, which advantageously makes the extremity offloading system 10 biocompatible. In some examples, the first component 20 and/or the second component 40 can be made of or coated with a water repellent material or coating. Advantageously, forming the components 20 and 40 with or coating the components with water repellant material enables the extremity offloading system 10 to be made wet, such as from perspiration or water, or other bathing solution, without damaging the extremity offloading system 10. In some examples, the first component 20 and/or the second component 40 can be made of a foam with a density between 1 lb/ft$^3$ to 26 lb/ft$^3$, and in some examples between 1 lb/ft$^3$ to 10 lb/ft$^3$ or between 3 lb/ft$^3$ to 6 lb/ft$^3$.

Figure 5:
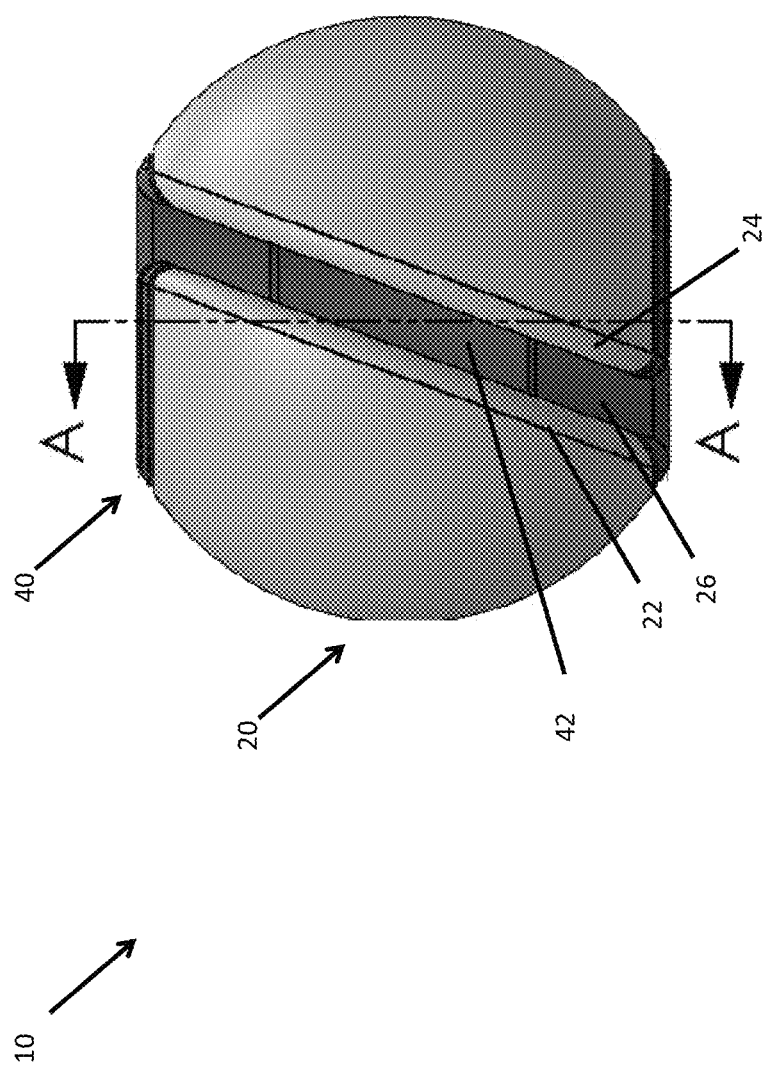
FIG. 5 illustrates an anterior view of the extremity offloading system of FIGS. 1-4.

The first component 20 can have a longitudinal axis extending along the length of the first component 20 can extend between a proximal end and a distal end. As shown in FIG. 5, the first component 20 can have a first opening 26 that extends through the first thickness of the first component 20 on the front or anterior side of the first component 20. The first opening 26 can extend from the outer surface 28 to the inner surface 30. In this manner, the opening 26 provides access to the central aperture defined by the inner surface 30. In this manner, the outer surface 28 and the inner surface 30 are discontinuous along the circumference of the extremity offloading system 10. The opening 26 can extend from the proximal end to the distal end of the first component 20. The first opening 26 can be straight, such that it is substantially parallel to the longitudinal axis of the first component 20. As illustrated in FIG. 5, the opening 26 can be slanted or angled, such that it is slanted or angled relative to the longitudinal axis of the first component 20. In some embodiments, the slant or angle of the opening can be 5 degrees, 10 degrees, 15 degrees, 20 degrees, 25 degrees, 30 degrees, 35 degrees, 40 degrees, or 45 degrees, or any angle in between the foregoing or lesser or greater than the foregoing. The first component 20 can have a first edge 22 and a second edge 24 wherein the space between the first edge 22 and the second edge 24 define the first opening 26. The first edge 22 can be considered a medial edge. The second edge 24 can be considered a lateral edge. In some examples, the medial edge and the lateral edge may be reversed. The first edge 22 can be parallel to the second edge 24. The first edge 22 can be separated from the second edge 24 to define the first opening 26. In some examples, the first edge 22 and the second edge 24 can each be beveled. The beveled edges can advantageously allow the first component 20 and the second component 40 to remain secured to the patient. In some examples, the first edge 22 and the second edge 24 can each be straight edges.

Similarly, the second component 40 can have a longitudinal axis extending along the length of the second component 40 and can extend from a bottom portion or end to a top portion or end. As shown, the second component 40 can be a cylinder with the proximal end and the distal end each being flat. The proximal end can be considered the top end. The distal end can be considered the bottom end. Furthermore, in some embodiments, the proximal end and distal end may be reversed. The second component 40 can have a second opening 46 that extends through the second thickness of the second component 40. The second opening 46 can extend from the outer surface 48 to the inner surface 50. In this manner, the opening 46 provides access to the central aperture defined by the inner surface 50. The opening 46 can extend from the proximal end to the distal end of the second component 40. The second opening 46 can be straight or curved. The opening 46 can be slanted or angled, such that it is slanted or angled relative to the longitudinal axis of the second component 40. In some embodiments, the slant or angle of the opening can be 5 degrees, 10 degrees, 15 degrees, 20 degrees, 25 degrees, 30 degrees, 35 degrees, 40 degrees, or 45 degrees, or any angle in between the foregoing or lesser or greater than the foregoing. The second component 40 can have a first edge 42 and a second edge 44. The first edge 42 can be considered a medial edge. The second edge 44 can be considered a lateral edge. In some examples, the medial edge and the lateral edge may be reversed. The first edge 42 can be parallel to the second edge 44. The first edge 42 can be separated from the second edge 44 to define the first opening 26.

The first opening 26 of the first component 20 can match or substantially match the second opening 46 of the second component 40, such that the first opening 26 and the second opening 46 are aligned when the second component 40 is inserted into the first component 20. In this way, the first opening 26 and the second opening 46 can be configured to open and close together when the extremity offloading system 10 is being handled, applied, or repositioned.

The extremity offloading system 10 can be configured to receive a portion of a leg or ankle 60 of a patient. As shown in FIG. 8A, in the open position, the extremity offloading system 10 can be opened to receive the portion of a leg or ankle 60. In the open position, the first edge 22 and the second edge 24 of the first component can be in widened or separated. The first edge 22 and the second edge 24 of the first component 20 can be separated to widen or increase the size of first opening 26. Similarly, the first edge 42 and the second edge 44 of the second component 40 can be separated to widen or increase the size of the second opening 46. The material of the first component 20 and the second component 40 can be flexible enough to allow the openings 26, 46 to be opened and be resilient enough to close the openings 26, 46 to secure the extremity offloading system 10 to the patient. The openings 26, 46 may automatically close when released by a user, or may be manually closed by the user. In some embodiments, the first opening 26 and second opening 46 can be configured to open and close together. In some embodiments, the first opening 26 and the second opening 46 can be configured to open and close independently from one another.

As the patient's leg or ankle 60 is inserted through the first opening 26 and the second opening 46, the patient's leg or ankle 60 may then be inserted in the space or aperture of the extremity offloading system 10. As described above, the space or aperture may be defined by the inner surface 50 of the second component 20. The inner surface 50 of the second component 20 can be configured to at least partially wrap around the portion of the patient's leg or ankle 60. The patient's leg or ankle 60 being inserted to the central space or aperture of the extremity offloading system 10 can cause closure of the extremity offloading system 10. This advantageously allows the extremity offloading system 10 to secure to the patient's leg or ankle 60 without the use of straps or other closure components. Without the use of straps or other closure components, the chances of error in installation or application of the extremity offloading system 10 is reduced, which can increase patient compliance and reduce injuries. The ease of application and securement can be done by one healthcare worker as opposed to some other systems which may require multiple people to apply. This can also reduce the need for a caretaker to continually monitor or adjust the extremity offloading system 10 on the patient.

Furthermore, the gravity or weight of the patient's leg or ankle 60 within the central aperture can not only close the extremity offloading system 10, but the gravity or weight of the patient's leg or ankle 60 can keep the extremity offloading system 10 closed. This advantageously allows the extremity offloading system 10 to be positioned on and retained on a patient's leg or ankle 60 without the use of fasteners or straps, thus making it easier and more convenient to position on/around and/or remove from an extremity of the patient. Further, the improved ease of using or positioning and removing the extremity offloading system 10 may result in improved patient compliance with maintaining use and positioning of the extremity offloading system 10. The overall spherical shape of the extremity offloading system 10 and curvature of the outer surface 28 advantageously allows for gravity to maintain the device in its proper position.

Additionally, the slanted openings along the length of the extremity offloading system 10 allows for easy application of the device for ease and comfort in application and to prevent inadvertent removal of the extremity offloading system 10.

Figure 8B:
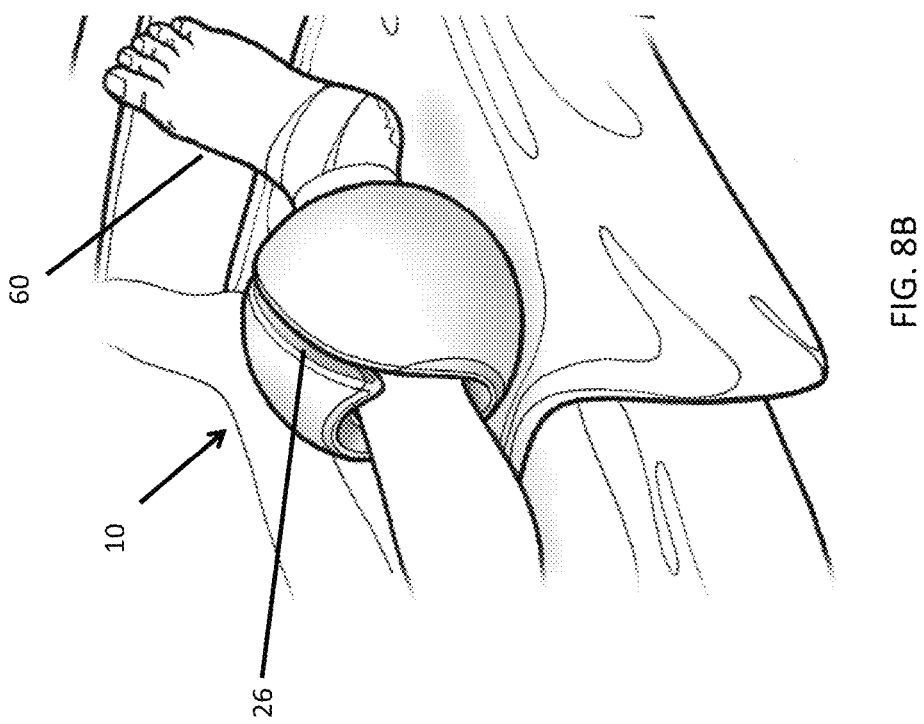
FIG. 8B illustrates the extremity offloading system positioned on a leg of a patient in a closed position.
Figure 8A:
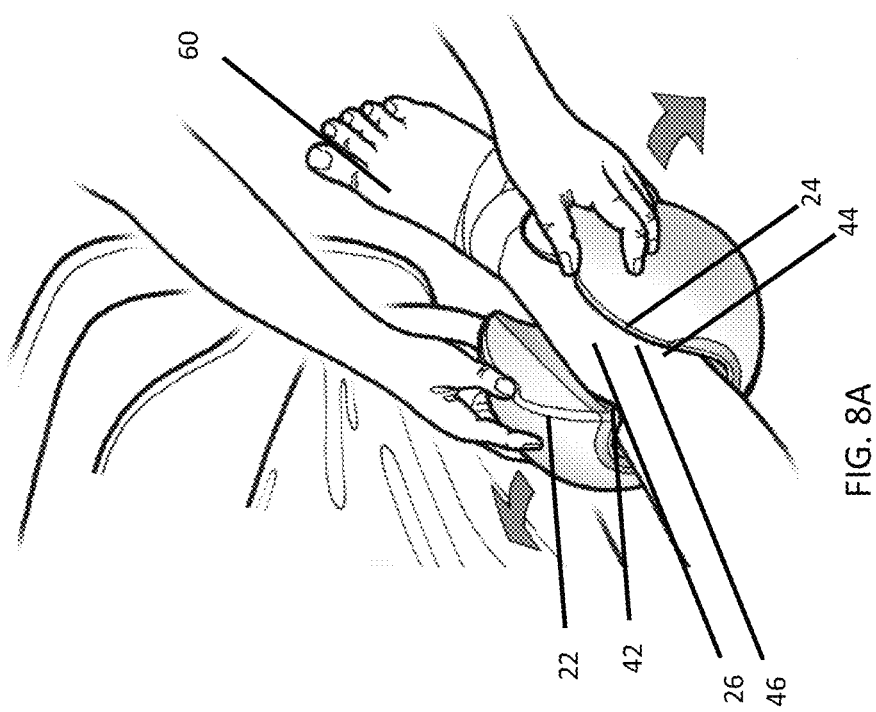
FIG. 8A illustrates the extremity offloading system positioned on a leg of a patient in an open position.

As shown in FIG. 8B, in the closed position, the extremity offloading system 10 can surround a portion of the patient's leg or ankle 60. In some examples, the extremity offloading system 10 can be used in patients at risk for DTPI. In some examples, the extremity offloading system 10 can also be used on an amputated limb or extremity, such as on a leg with a below knee amputation. Once a limb is amputated, a patient often puts excess pressure on the opposite limb, for example in order to shift in bed. This increased pressure on the non-amputated limb can subsequently develop into a DTPI. The extremity offloading system 10 can thus be used on either or both of the amputated limb and non-amputated limb. In the closed position, the first edge 22 and the second edge 24 of the first component 20 can be in close proximity or substantially closed. Similarly, the first edge 42 and the second edge 44 of the second component 40 can be in close proximity or substantially closed. In some examples, the first edge 22 and the second edge 24 can be in contact with one another in the closed position. Similarly, the first edge 42 and the second edge 44 of the second component 40 can be in contact with one another in the closed position. In some examples, the first edge 22 and the second edge 24 of the first component 20 as well as the first edge 42 and the second edge 44 of the second component 40 can be minimally separated. For example, the first opening 26 can be between 0.5 mm to 2 mm, such as between 0.5 mm to 1 mm, 1 mm to 1.5 mm, or 1.5 mm to 2 mm in the closed position. It should be understood that the dimensions are not limited as such and the first opening 26 can be lesser or greater than the disclosed examples.

As shown in FIG. 8B, when the extremity offloading system 10 is secured to the patient's leg or ankle 60 and the patient's leg is resting substantially parallel to a surface, the extremity offloading system 10 elevates or suspends the patient's heel, thus reducing the weight applied to the back of a patient's heel.

As shown in FIGS. 9-14 and 16-35, the extremity offloading system 100 can include a body 110, which can have a spherical shape. The extremity offloading system 100 can also be a unitary structure, as in one-piece. Similar to the extremity offloading system 10, the extremity offloading system 100 can also be called a support system, a support assembly, a suspension system, a suspension assembly or a sphere for an extremity, limb, or heel. The body 110 can have an outer surface 118 that is spherical or round or at least partially spherical or round. As shown, the proximal end 112 and the distal end 114 can each be flat, such that the body 110 does not form a full sphere. The proximal end 112 can be considered the top end. The distal end 114 can be considered the bottom end. Furthermore, in some embodiments, the proximal end 112 and distal end 114 may be reversed. The body 110 can have a thickness between the inner surface 130 and the outer surface 118.

Figure 10:
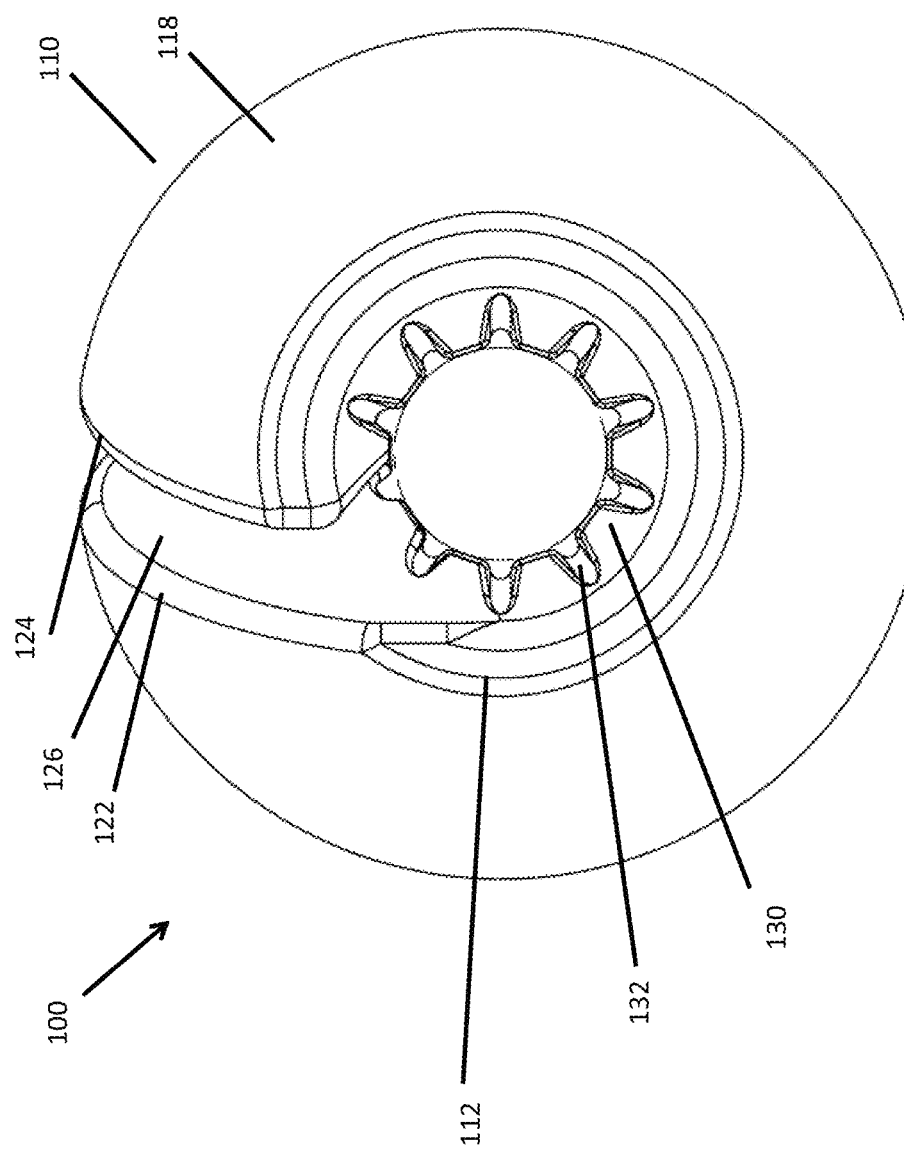
FIG. 10 illustrates a top view of the extremity offloading system of FIG. 9.
Figure 13:
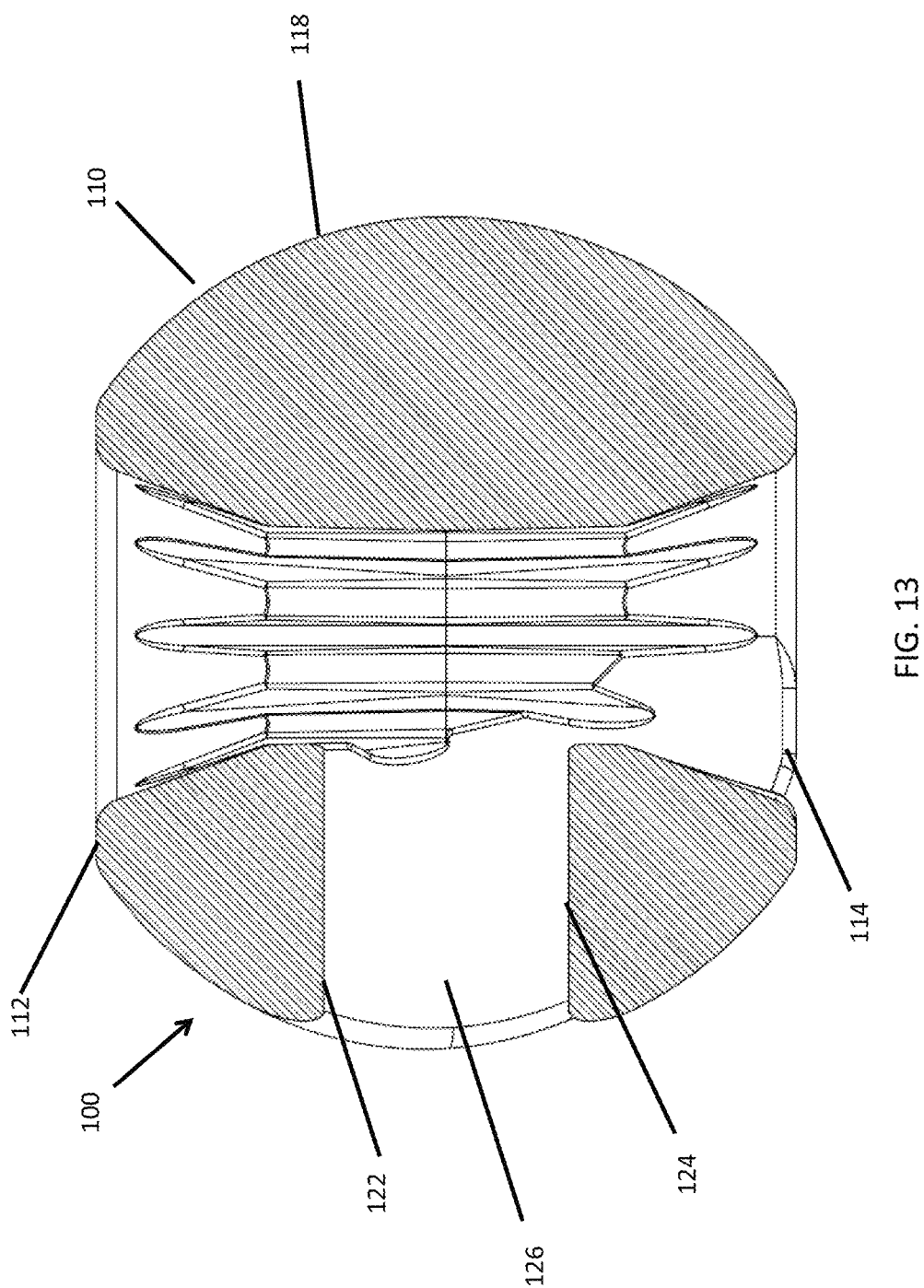
FIG. 13 illustrates a cross-sectional view along a length of the extremity offloading system at line 13-13 of FIG. 12.
Figure 14:
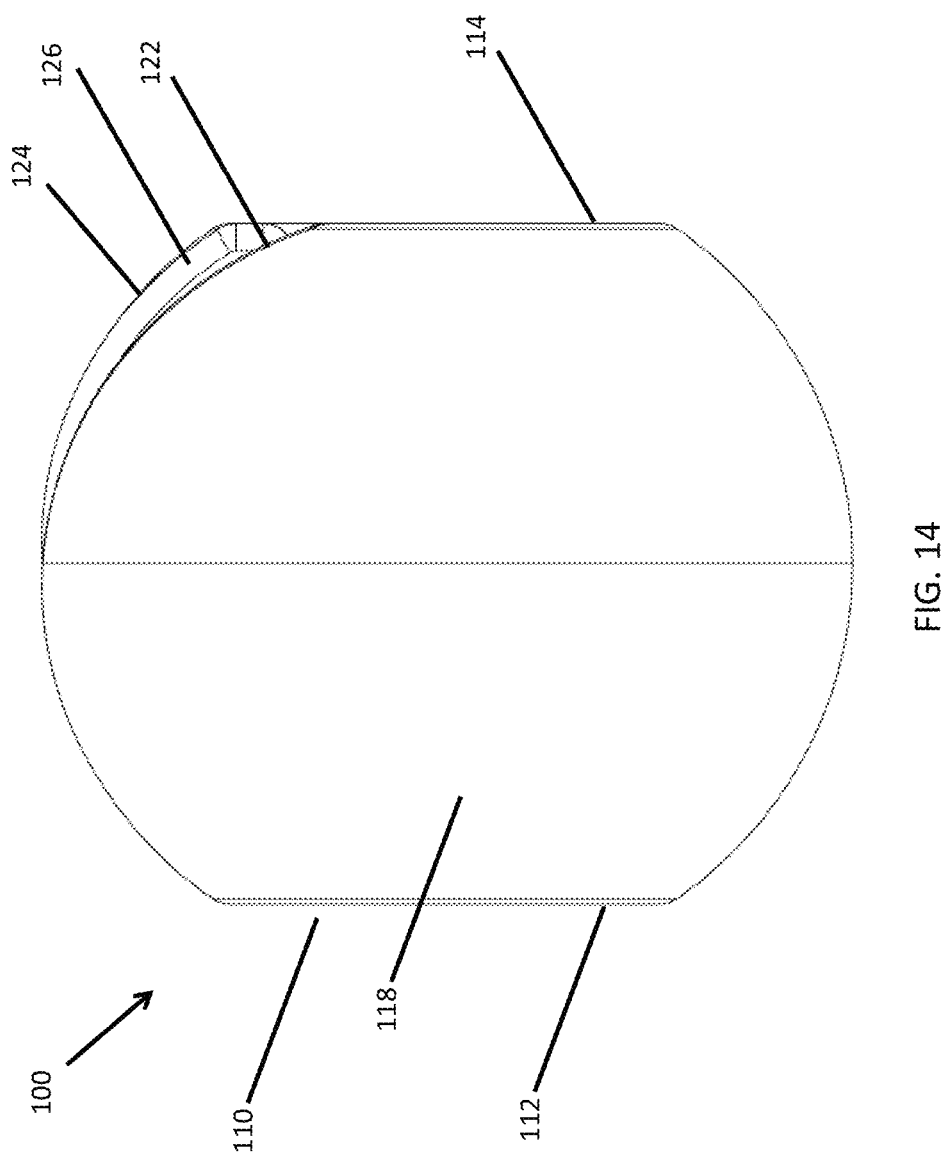
FIG. 14 illustrates a side view of the extremity offloading system of FIGS. 9-13.
Figure 15:
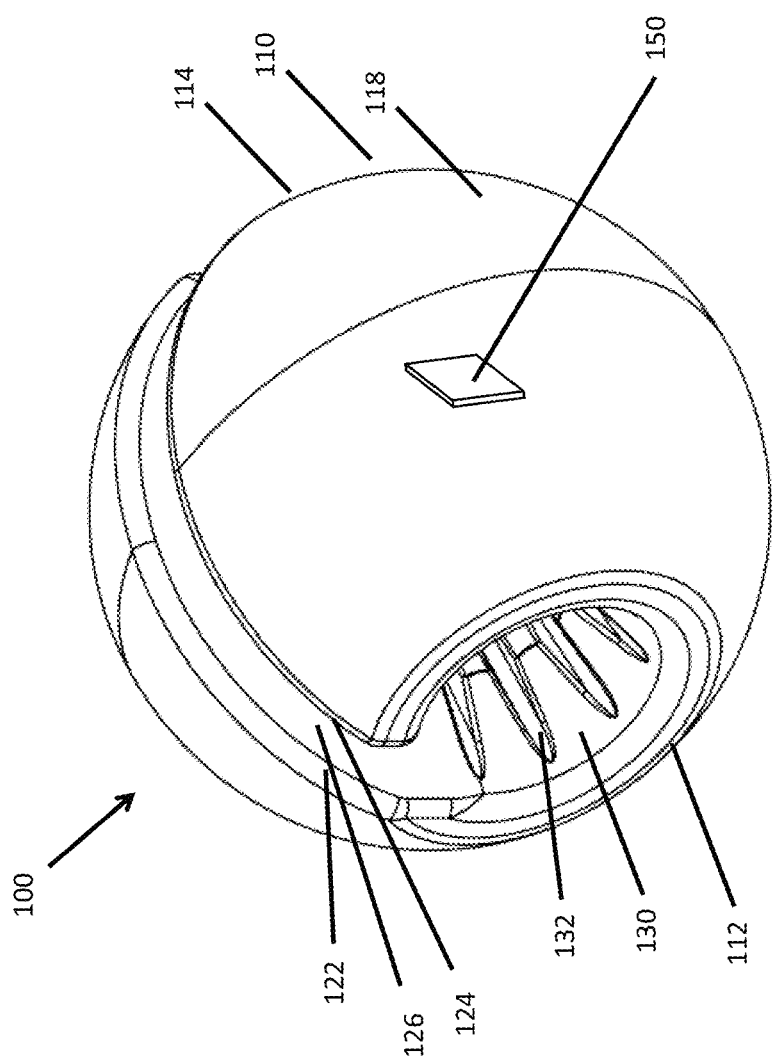
FIG. 15 illustrates a perspective view of yet another embodiment of a extremity offloading system with a circuit.
Figure 16:
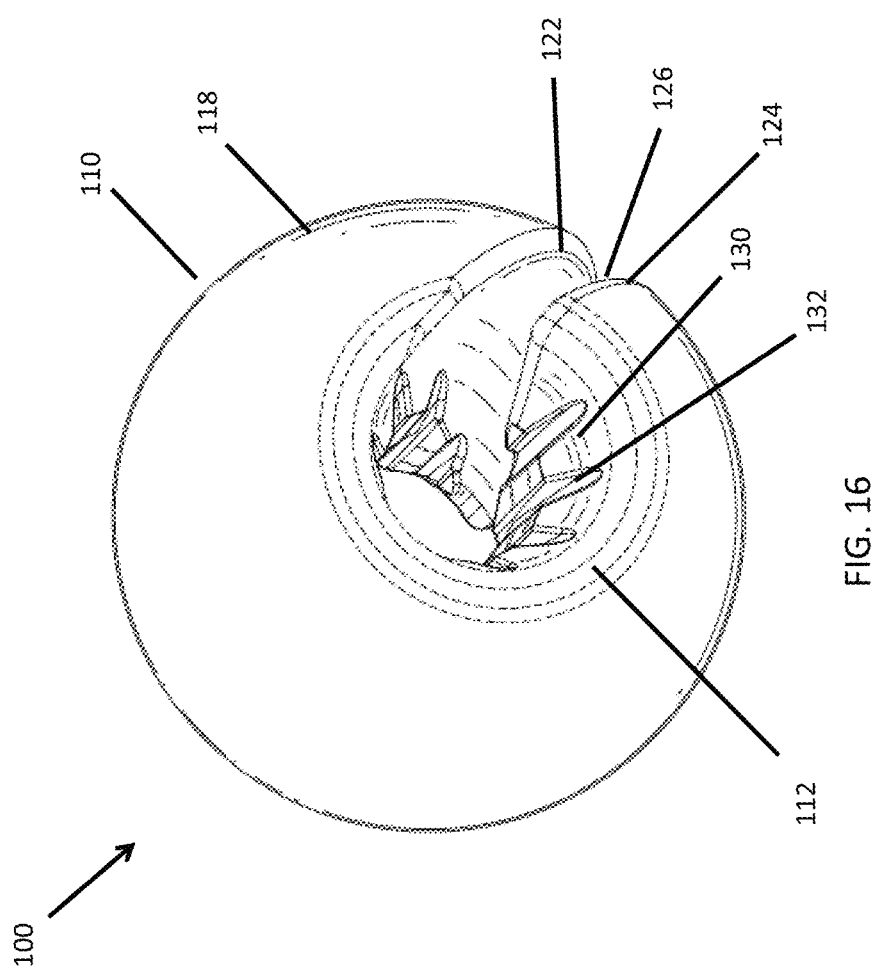
FIG. 16 illustrates a perspective view of yet another embodiment of a extremity offloading system.
Figure 17:
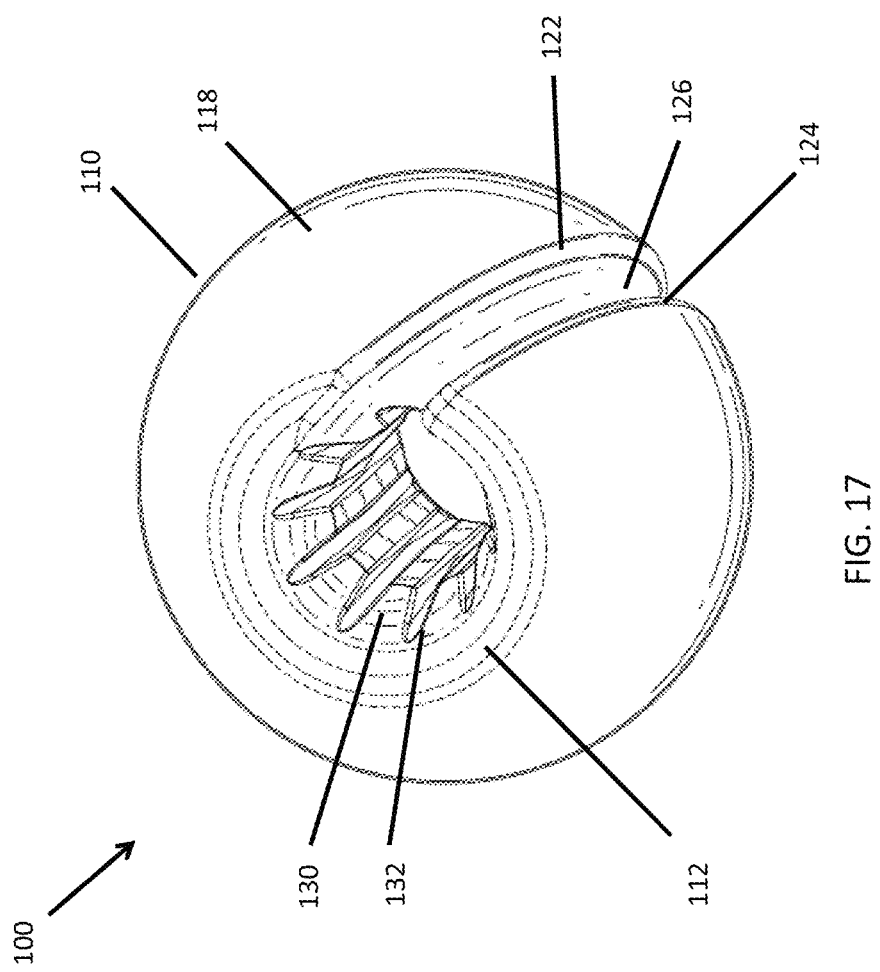
FIG. 17 illustrates another perspective view of the extremity offloading system of FIG. 16.
Figure 18:
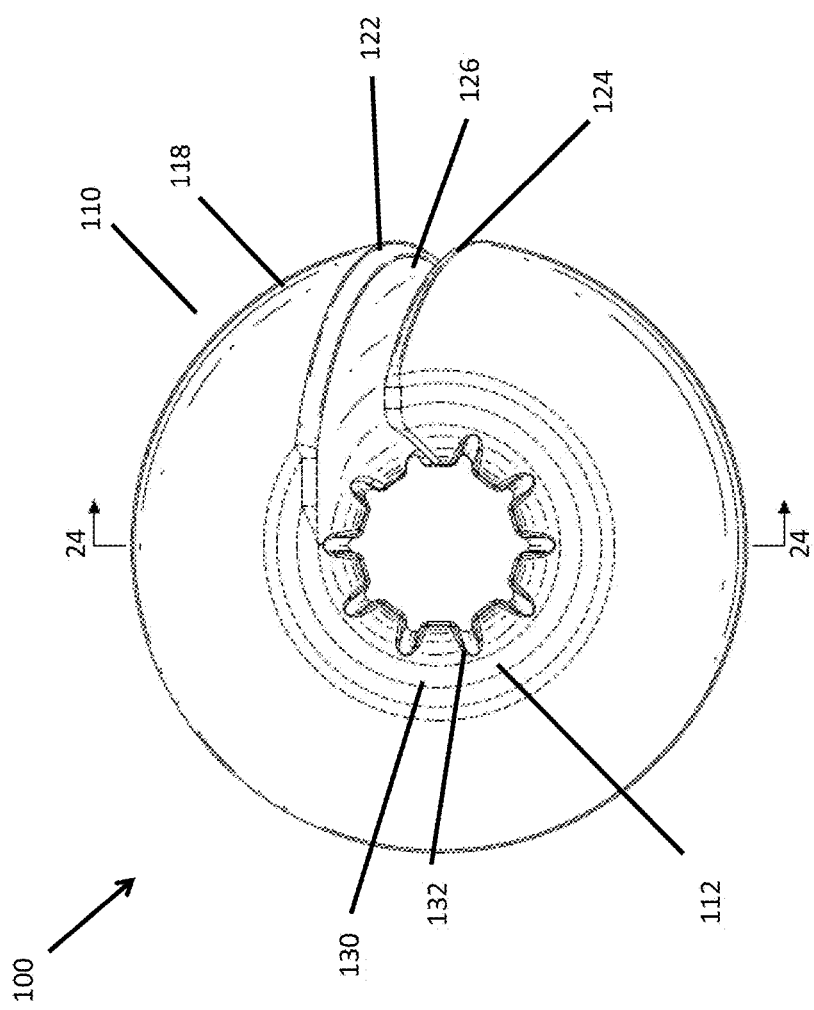
FIG. 18 illustrates a front view of the extremity offloading system of FIGS. 16-17.
Figure 19:
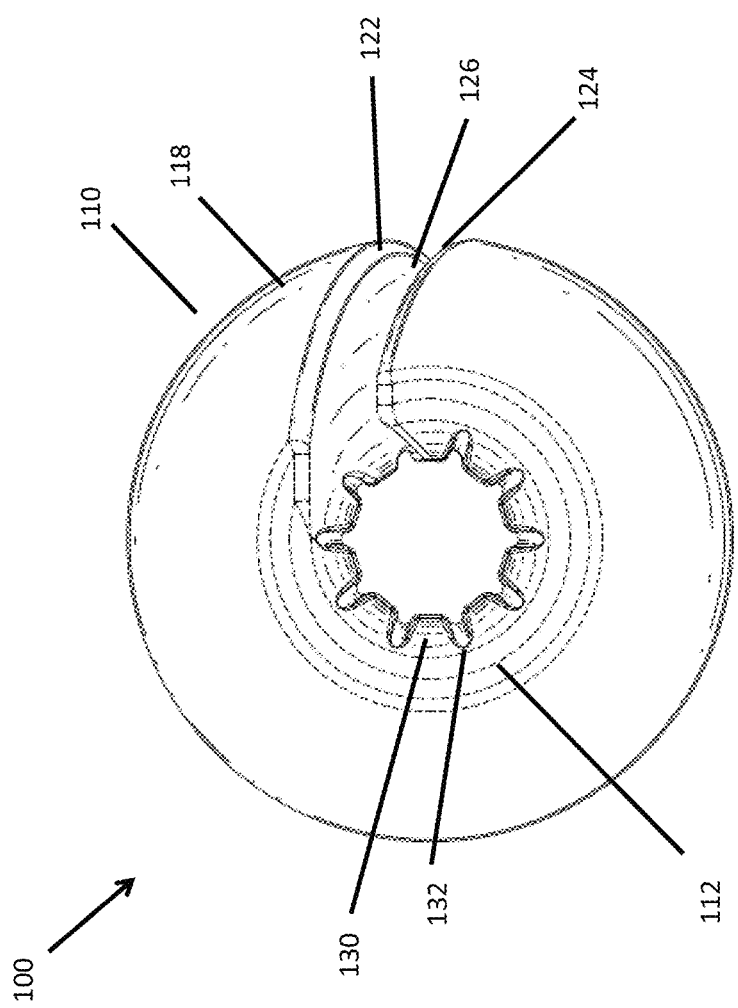
FIG. 19 illustrates a rear view of the extremity offloading system of FIGS. 16-18.
Figure 20:
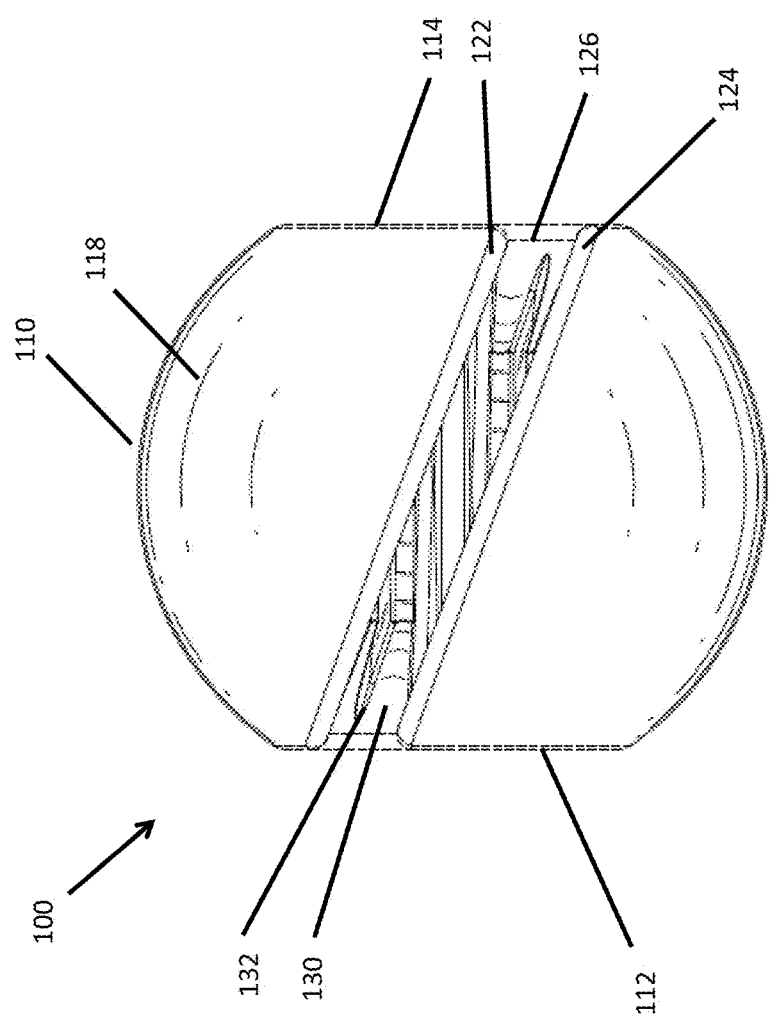
FIG. 20 illustrates a right side view of the extremity offloading system of FIGS. 16-19.
Figure 21:
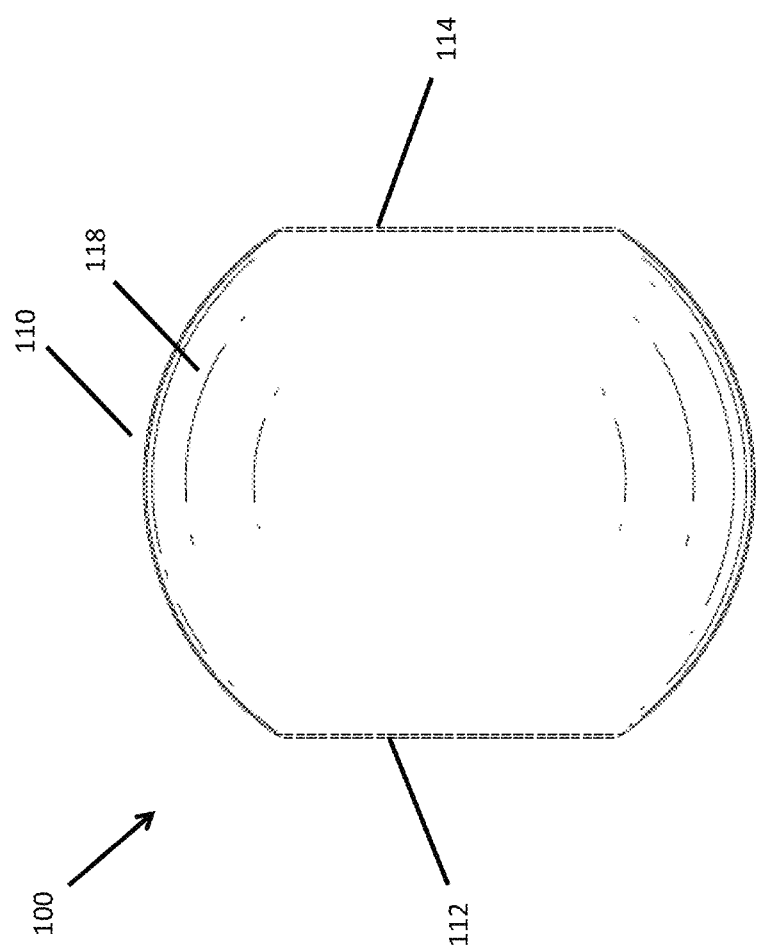
FIG. 21 illustrates a left side view of the extremity offloading system of FIGS. 16-20.
Figure 22:
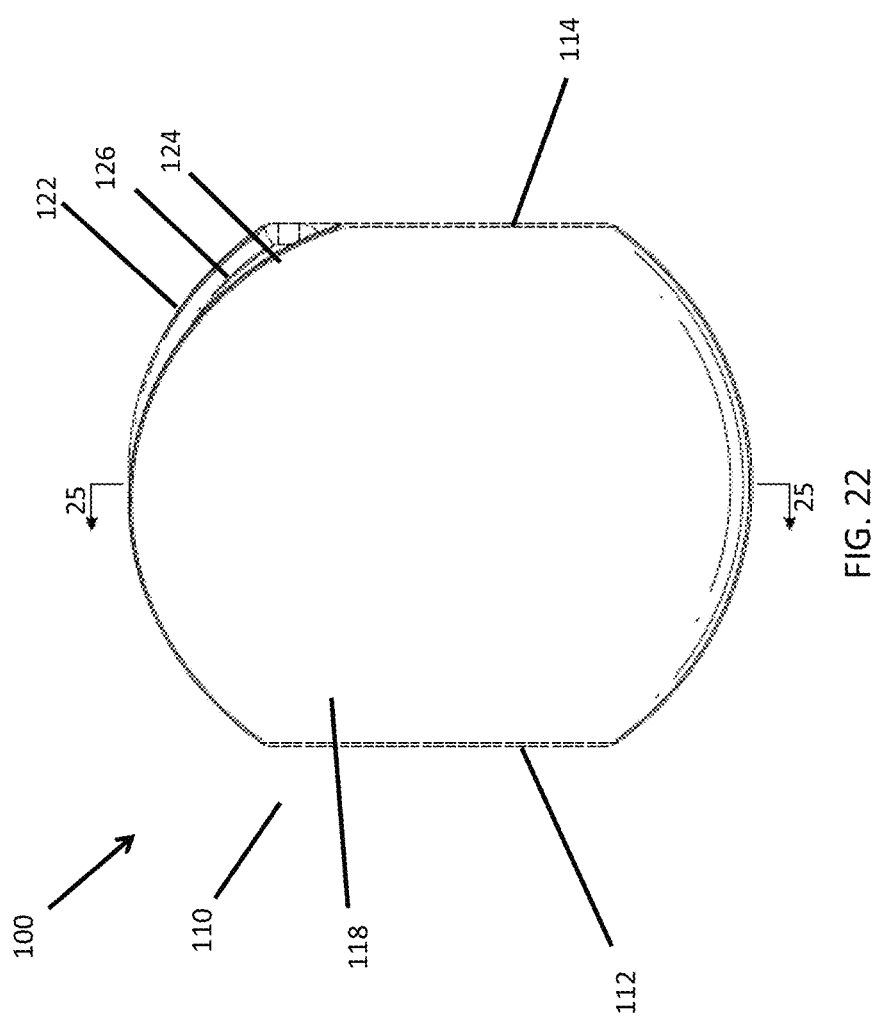
FIG. 22 illustrates a top view of the extremity offloading system of FIGS. 16-21.
Figure 23:
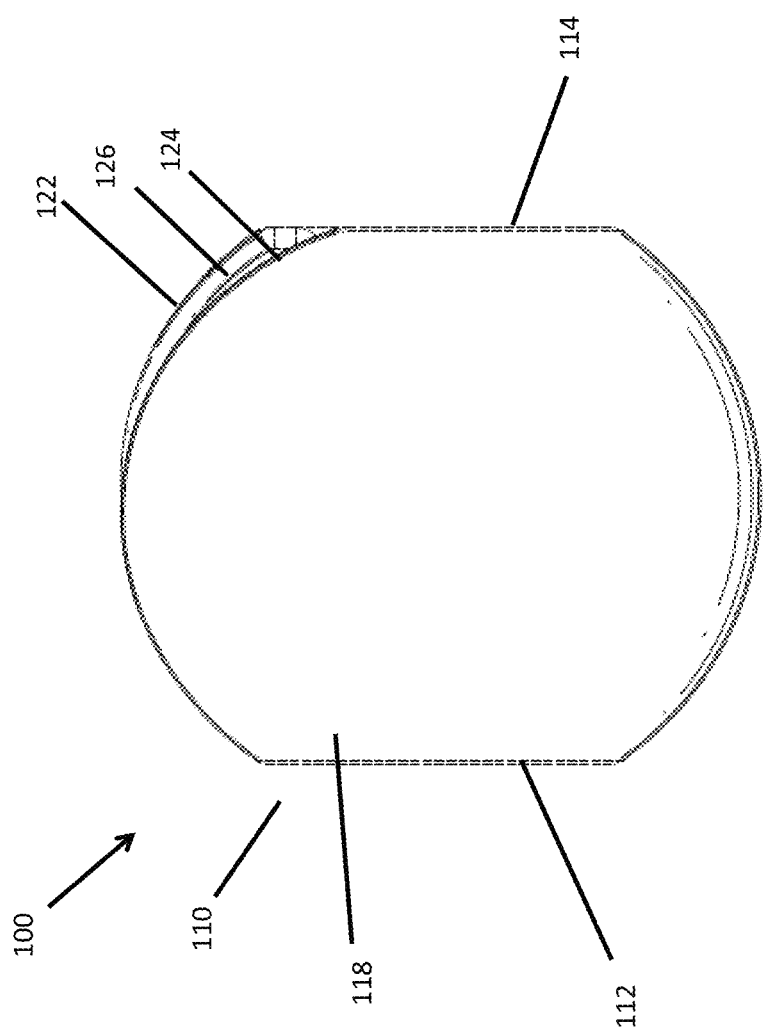
FIG. 23 illustrates a bottom view of the extremity offloading system of FIGS. 16-22.
Figure 24:
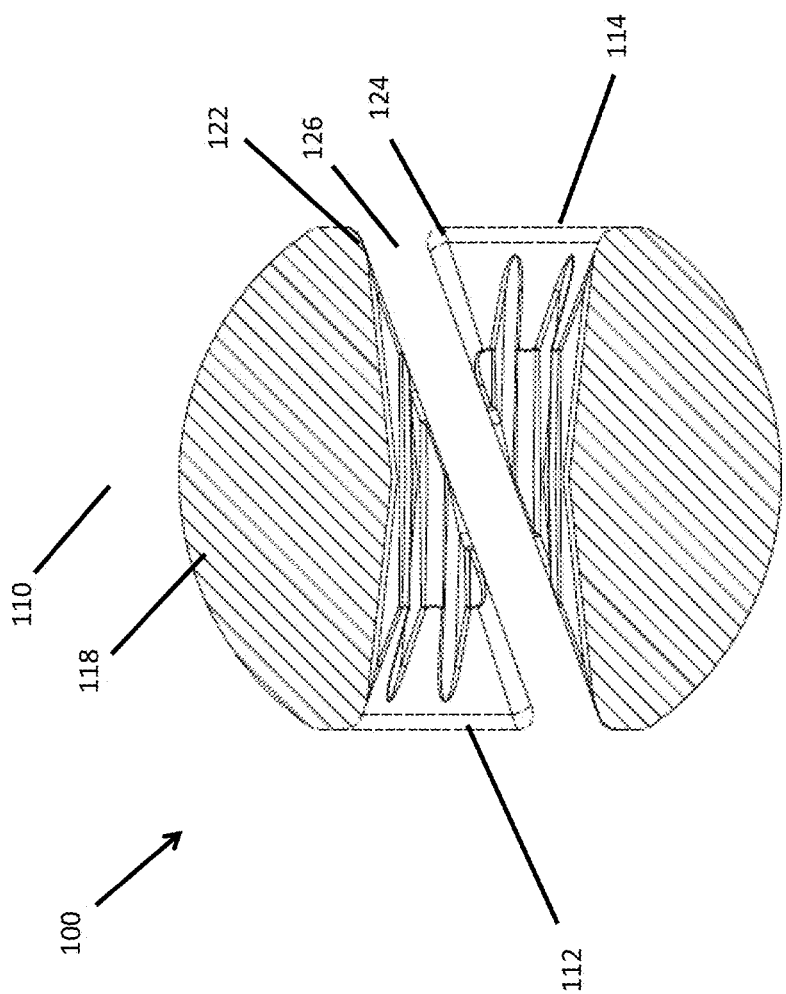
FIG. 24 illustrates a sectional view through the line 24-24 in FIG. 18.
Figure 25:
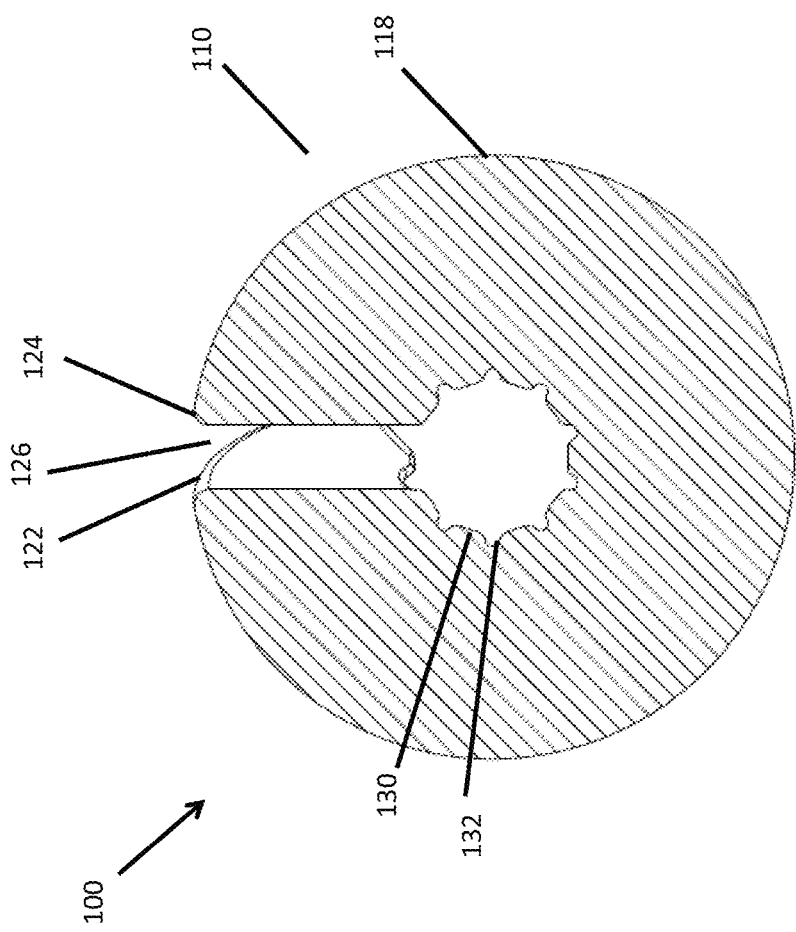
FIG. 25 illustrates a sectional view through the line 25-25 in FIG. 22.
Figure 26:
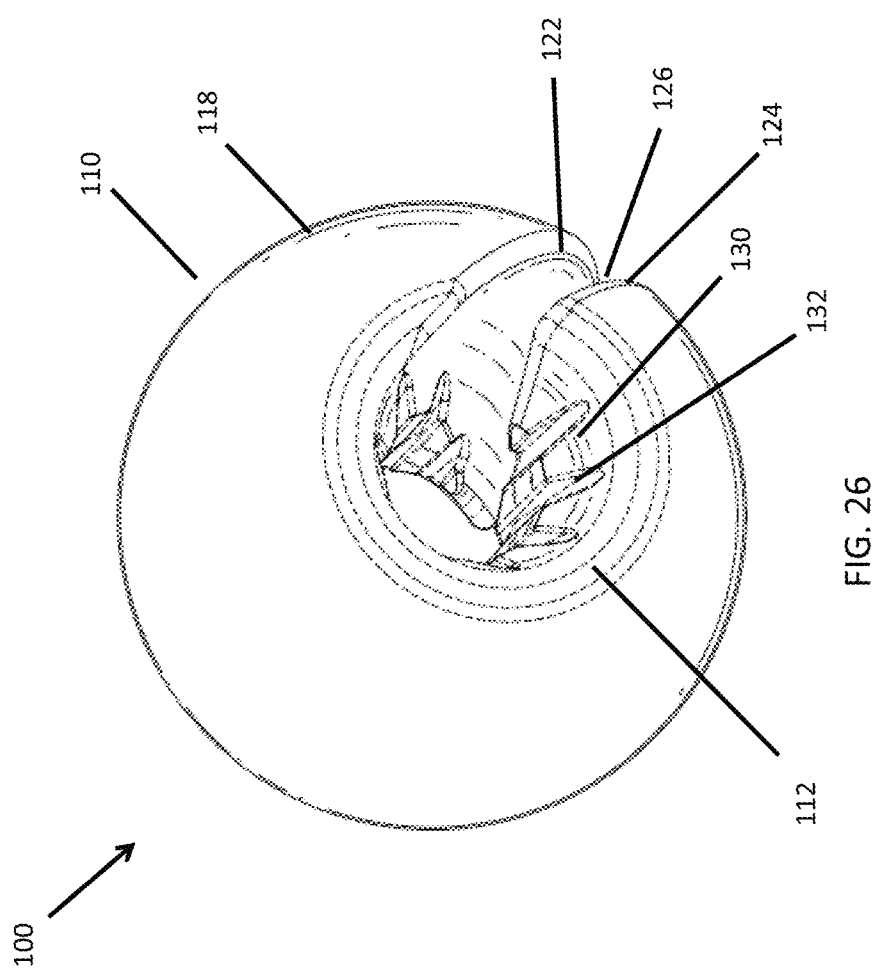
FIG. 26 illustrates a perspective view of yet another embodiment of a extremity offloading system.
Figure 27:
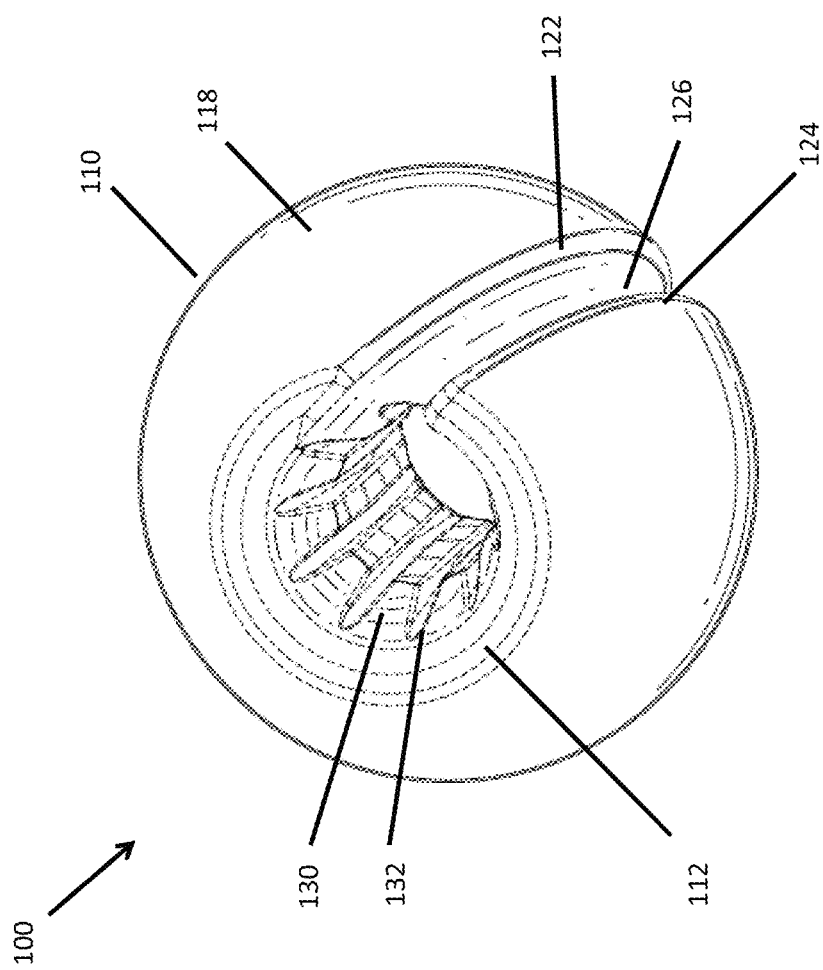
FIG. 27 illustrates another perspective view of the extremity offloading system of FIG. 26.
Figure 28:
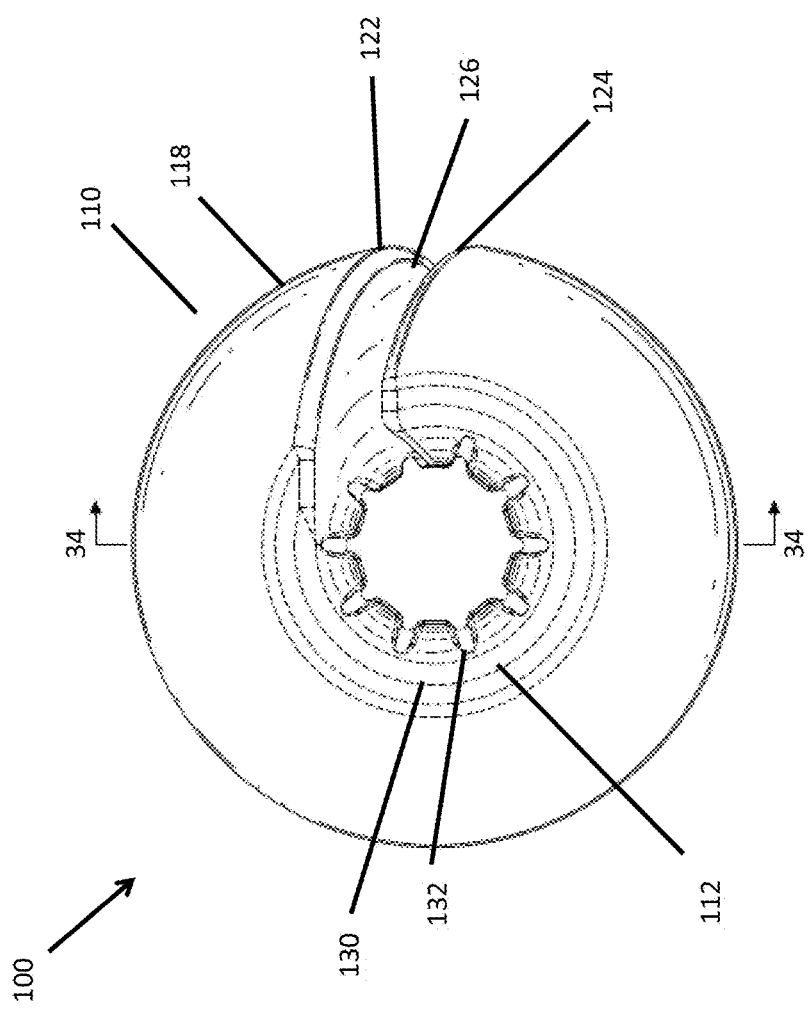
FIG. 28 illustrates a front view of the extremity offloading system of FIGS. 26-27.
Figure 29:
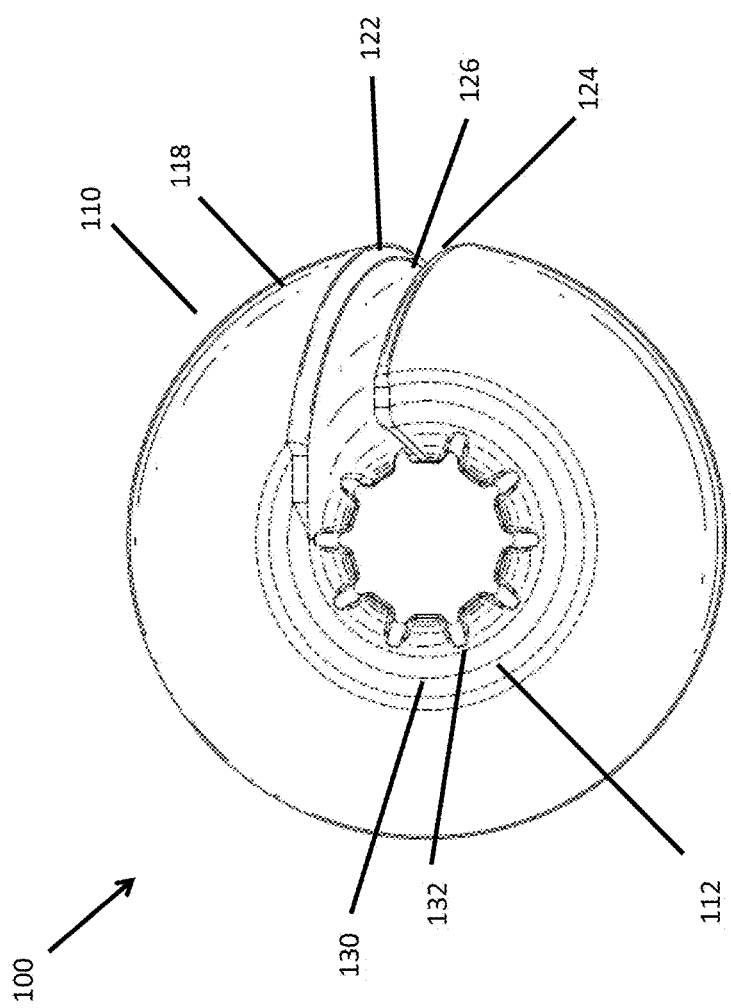
FIG. 29 illustrates a rear view of the extremity offloading system of FIGS. 26-28.
Figure 30:
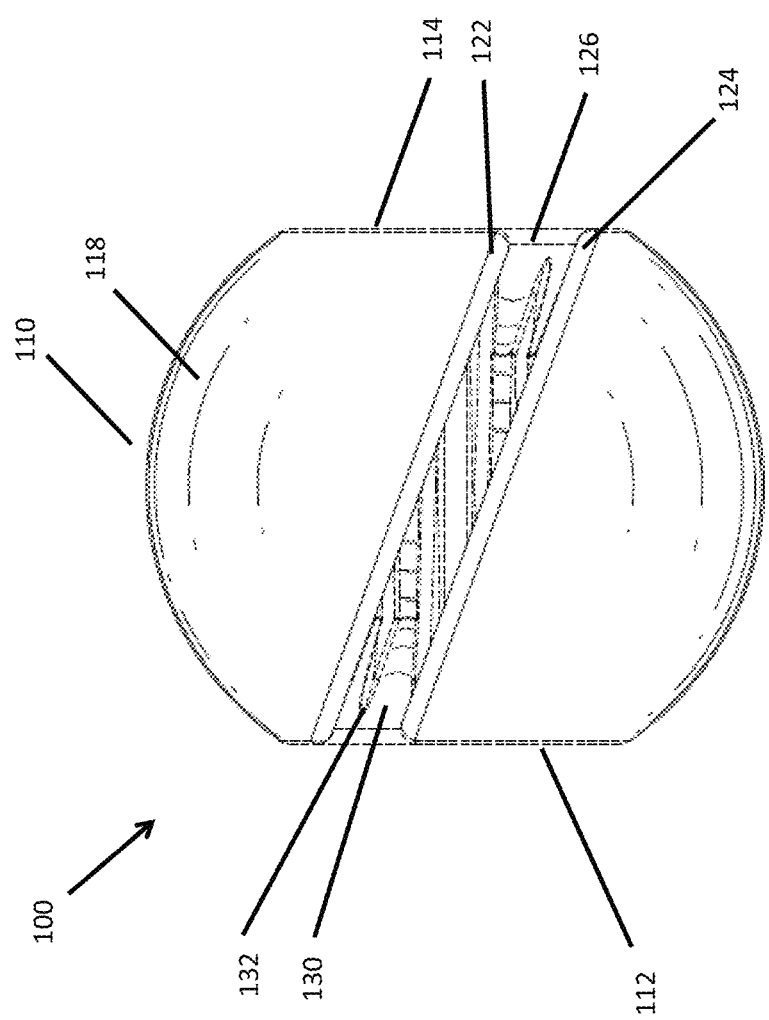
FIG. 30 illustrates a right side view of the extremity offloading system of FIGS. 26-29.
Figure 31:
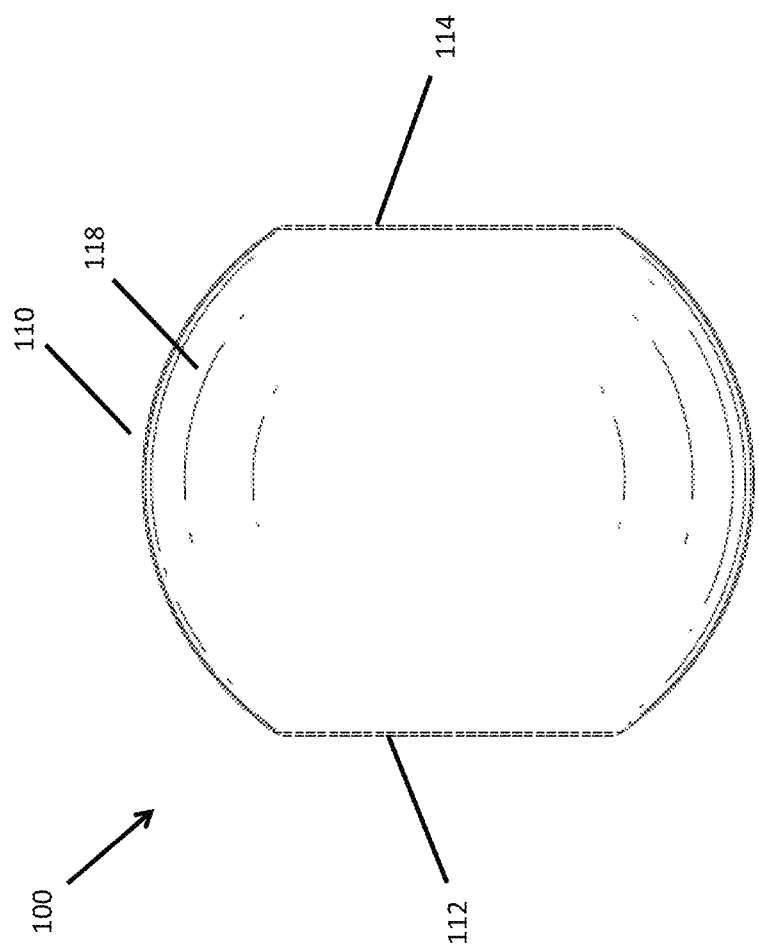
FIG. 31 illustrates a left side view of the extremity offloading system of FIGS. 26-30.
Figure 32:
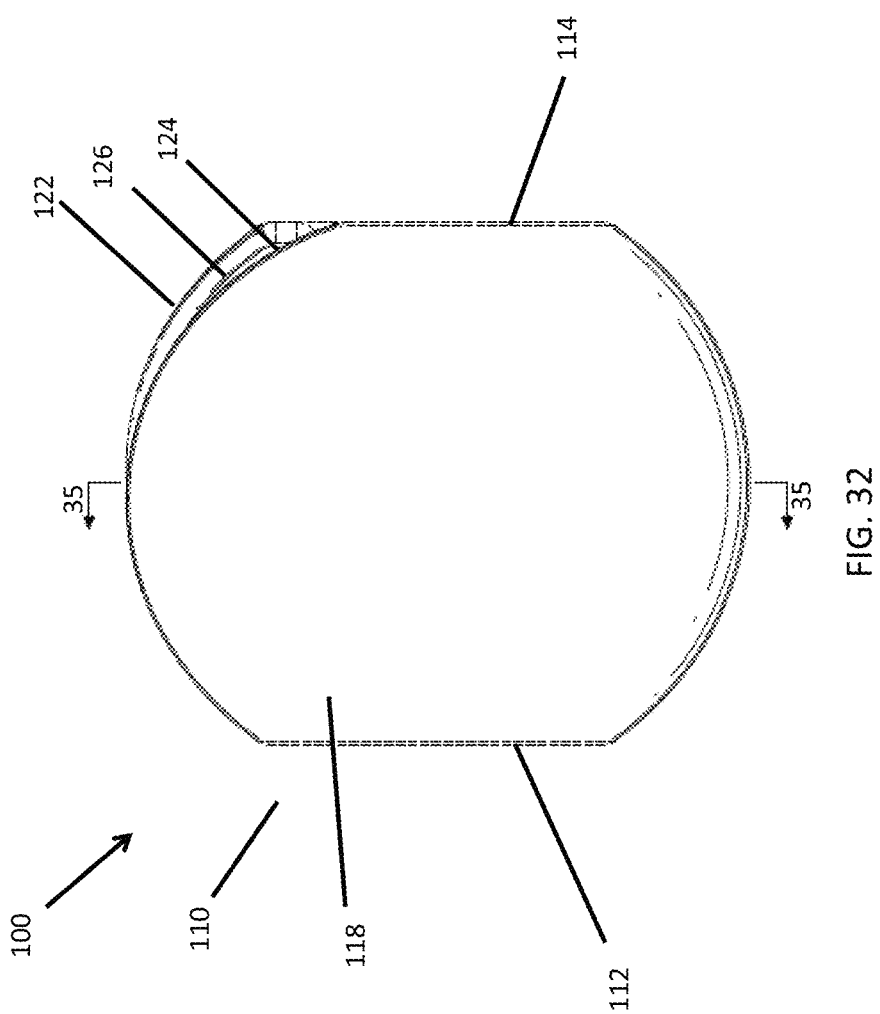
FIG. 32 illustrates a top view of the extremity offloading system of FIGS. 26-31.
Figure 33:
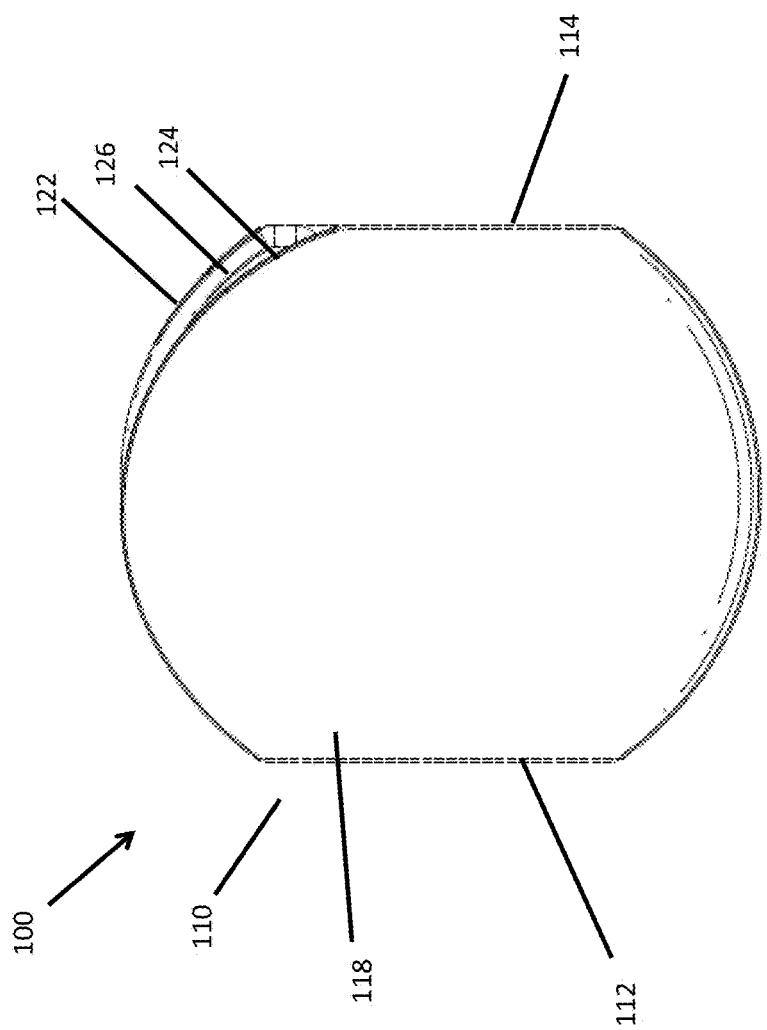
FIG. 33 illustrates a bottom view of the extremity offloading system of FIGS. 26-32.
Figure 34:
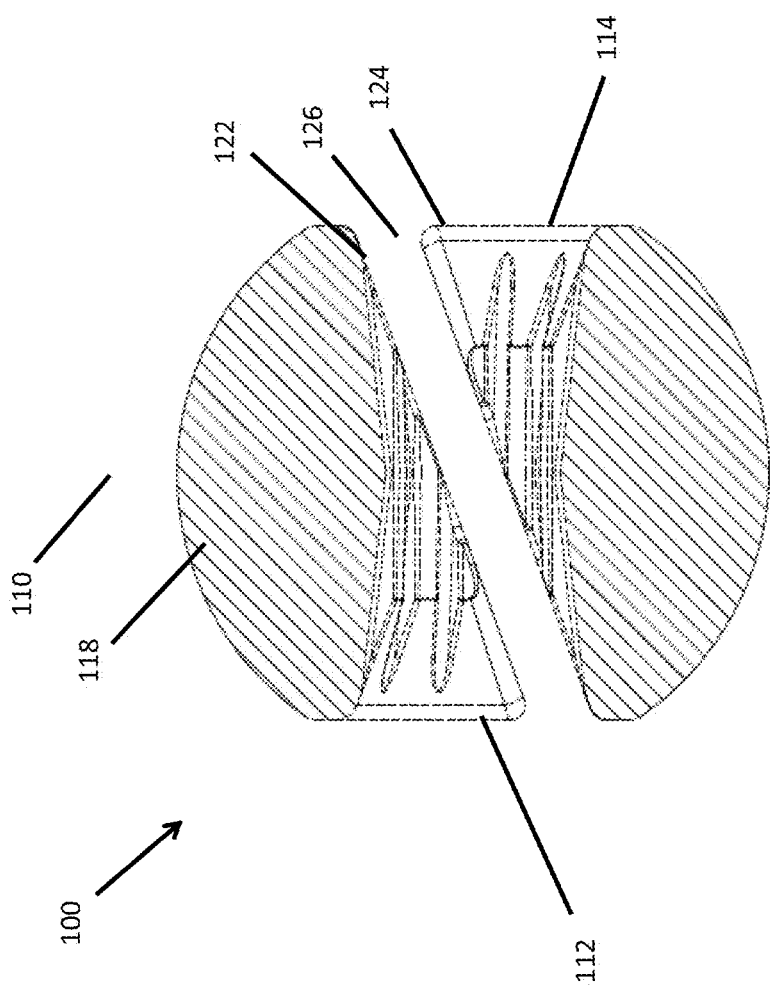
FIG. 34 illustrates a sectional view through the line 34-34 in FIG. 28.
Figure 35:
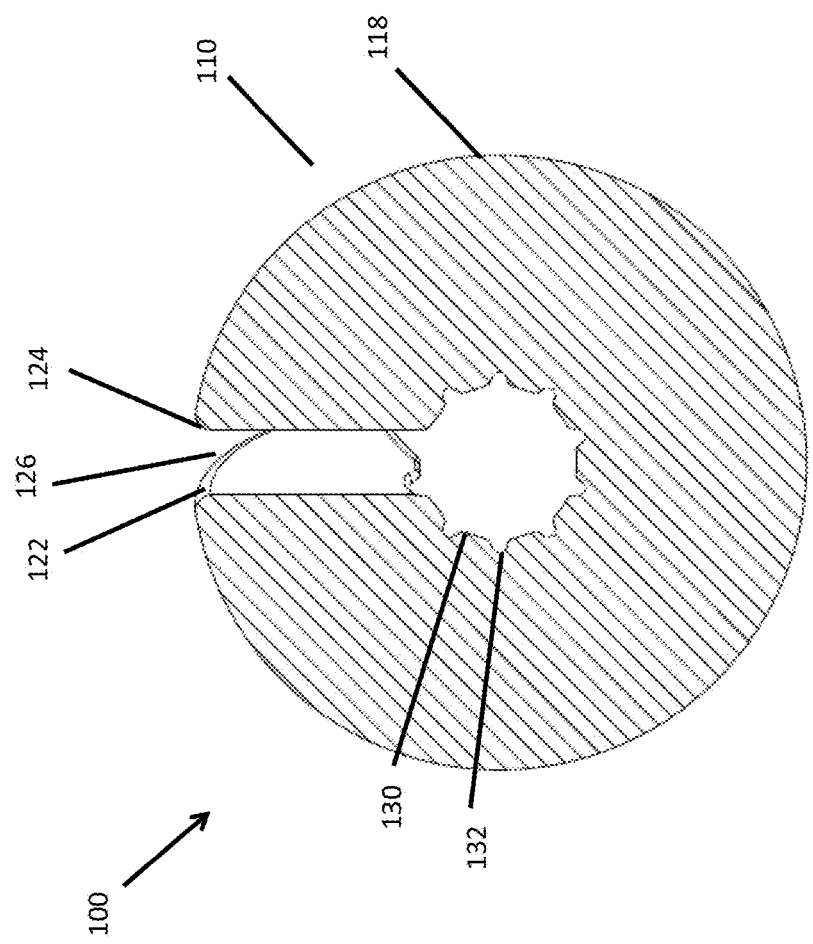
FIG. 35 illustrates a sectional view through the line 35-35 in FIG. 32.

The body 110 can also have a central or first aperture that is defined by the inner surface 130. The inner surface 130 can be cylindrical or at least partially cylindrical. In some examples, the central aperture defined by the inner surface 130 is a cylindrical or partially cylindrical aperture. As shown in FIG. 10, which illustrates a top or end view of the extremity offloading system 100, the central aperture can be a circle. In other examples, the central aperture can have different shapes, such as square, rectangular, triangular or another rounded shape (e.g. oval). The central aperture can extend from the first end to the second end along the length of the body 110, such as from the proximal end 112 to the distal end 114. As shown in FIG. 13, which illustrates a cross-sectional view along the length of the extremity offloading system 100, the central aperture of the body 110 can be rectangular in the cross sectional view at least along a portion of the length of the body 110. The first end and the second end of the central aperture of body 110 be angled, such that the diameter increases towards the proximal end 112 and the distal end 114 of the body 110. As shown in FIG. 13, the cross-sectional view of the central aperture of the body 110 can have a first end and a second end which are sloped or triangular in the cross-sectional view. For example, in some examples, the diameter of the central aperture of the body 110 can be a first diameter in the center or middle of the body 110. The diameter of the central aperture can increase towards the first end and the second end to a larger, second diameter. The diameter of the central aperture can gradually increase from the first diameter at the center to the second diameter at the first end or at the second end, such that the inner surface 130 can be sloped as the diameter increases.

The central aperture defined by the inner surface 130 which can receive the patient's leg or ankle. The central aperture can taper outward at the end, such that the diameter of the central aperture increases towards the proximal end 112 and the distal end 114 of the body 110. This can advantageously provide comfort to the patient when the extremity offloading system 100 is positioned on the patient. In other examples, the diameter of the central aperture can be constant along the length of the body 110.

In some examples, the length between the first end and the second end of the first component 20 can be between 2 to 10 inches, such as between 2 to 4 inches, 5 to 10 inches, such as between 5 to 6 inches, 6 to 7 inches, 7 to 8 inches, 8 to 9 inches, or 9 to 10 inches. In some examples, the outer diameter or width of the first component 20 can be between 5 to 15 inches, such as between 5 to 7 inches, 7 to 9 inches, 9 to 11 inches, 11 to 13 inches, or 13 to 15 inches. In some examples, the diameter of the central aperture of the body 120 can be between 5 to 15 inches, such as between 5 to 6 inches, 6 to 7 inches, 7 to 8 inches, 8 to 9 inches, 9 to 10 inches, 10 to 11 inches, 11 to 12 inches, 12 to 13 inches, or 14 to 15 inches. It should be understood that the dimensions are not limited as such and the lengths and/or diameters may be lesser or greater than the disclosed examples.

The body 110 can have a plurality of flutes or cutouts 132 along the inner surface 130 of the central aperture. Each of the plurality of flutes can have a length that extend along the length of the central aperture. The plurality of flutes 132 can extend along the circumference of the central aperture along the inner surface 130. The plurality of flutes 132 can be equally spaced around a circumference of the aperture defined by the inner surface 130. The plurality of flutes 132 are positioned along the inner surface 120 of the central aperture, such that each of the plurality of flutes are configured to be positioned against a patient's leg when the patient's leg is inserted in the central aperture. These flutes 132 can advantageously allow air to flow through the flutes 132 to provide comfort to the patient while the device is in use. For example, the flutes 132 allow air to flow which can prevent too much friction from occurring between the inner surface 130 and the patient's skin. The flutes 132 can also lower the temperature of the patient's leg with the device positioned thereon. The flutes 132 can also reduce moisture build up of the patient with the device positioned thereon. The body 110 can have any number of flutes, such as 6, 8, 10, 12, or 14 flutes. As shown, the body 110 can have 10 flutes, which can advantageously provide adequate air flow and support, while preventing the creation of too many pressure points for patient comfort.

Figure 11:
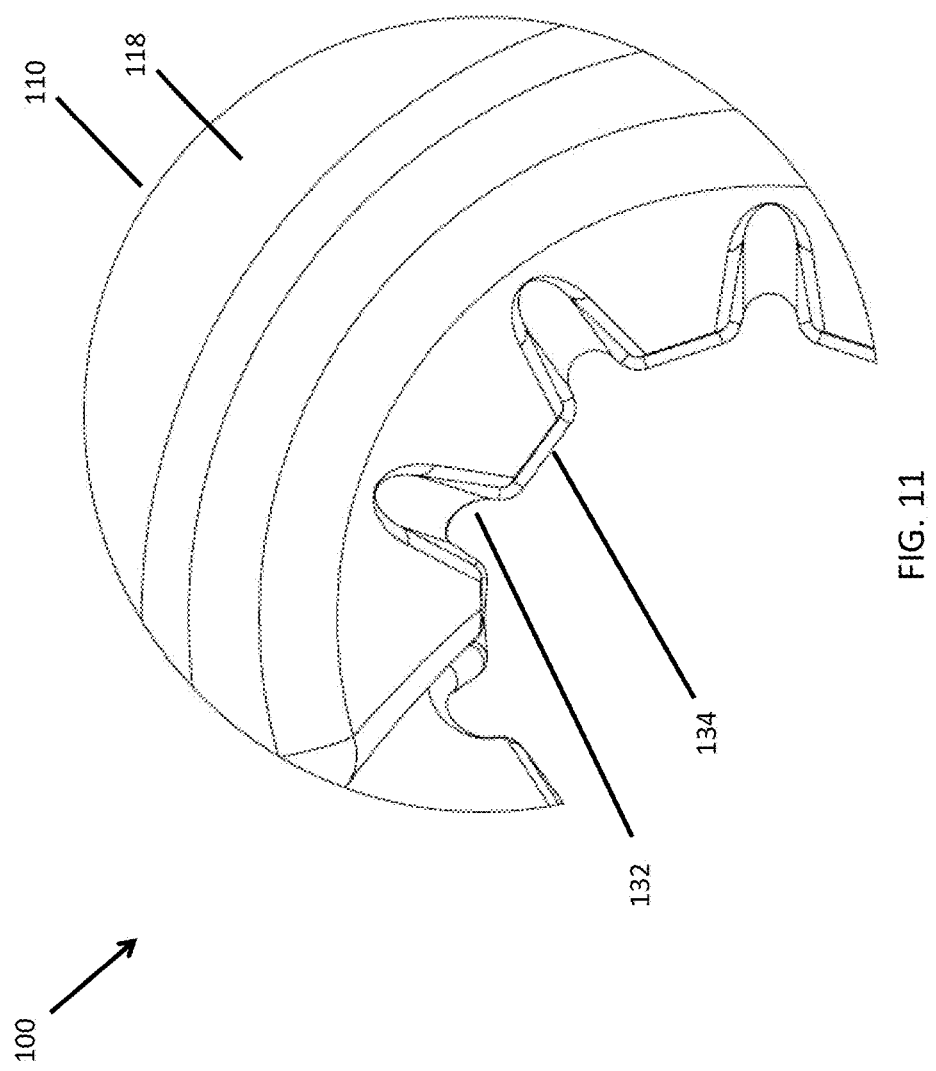
FIG. 11 illustrates a partial perspective view of the extremity offloading system of FIGS. 9-10.

There can be a plurality of portions 134 of the inner surface 130 between each of the plurality of flutes 132. For example, as shown in FIG. 11, the plurality of portions 134 can be flat portions or surfaces. The plurality of portions 134 being flat can advantageously allow for a more uniform surface, comfortable contact with the patient's skin, and better contact for any surfaces positioned therein. In other examples, the plurality of portions 134 can be triangular or rounded or any other shape. In some examples, as shown in FIG. 11, the corners between each of the portions 134 and the flutes 132 may be rounded. In some examples, the corners between each of the portions 134 and the flutes 132 may be sharp.

In some examples, the depth of each flute 132, which can be measured radially from the inner surface 130, can be between 0.1 to 1 inches, such as between 0.1 to 0.2 inches, 0.2 to 0.3 inches, 0.3 to 0.4 inches, 0.5 to 0.6 inches, 0.6 to 0.7 inches, 0.7 to 0.8 inches, 0.8 to 0.9 inches, or 0.9 to 1 inches. In some examples, the width of each flute 132, which can be measured at a base of each flute 132, can be between 1 to 5 inches, such as between 1 to 2 inches, 2 to 3 inches, 3 to 4 inches, or 4 to 5 inches. In some examples, the width of the flat surface of the plurality of portions 134 can be between 0.1 to 1 inch, such as between 0.1 to 0.3 inches, 0.3 to 0.5 inches, 0.5 to 0.7 inches, or 0.7 to 0.9 inches. In some examples, the angle between each of the flutes 132 can be between 15° to 45°, such as between 20° to 30° or between 30° to 40°. In some examples, the angle between each of the plurality of portions 134 can be between 15° to 45°, such as between 20° to 30° or between 30° to 40°.

The body 120 can be constructed from any material, such as foam. In some examples, the body 120 can made of memory foam. In some examples, the body 120 can be made of an antimicrobial or antibacterial material. In some examples, the material of the body 120 may include holes or may be made of a breathable material for the patient's comfort and to prevent infection. In some examples, the body 120 can be coated in a layer of an antimicrobial or antibacterial material. In some examples, the body 120 can be made of a material that is latex free, which advantageously makes the extremity offloading system 100 biocompatible. In some examples, the body 120 can be made of or coated with a water repellent material or coating. In some examples, the body 120 can be made of a foam with a density between 1 lb/ft$^3$ to 26 lb/ft$^3$, and in some examples between 1 lb/ft$^3$ to 10 lb/ft$^3$ or 3 lb/ft$^3$ to 6 lb/ft$^3$.

Figure 12:
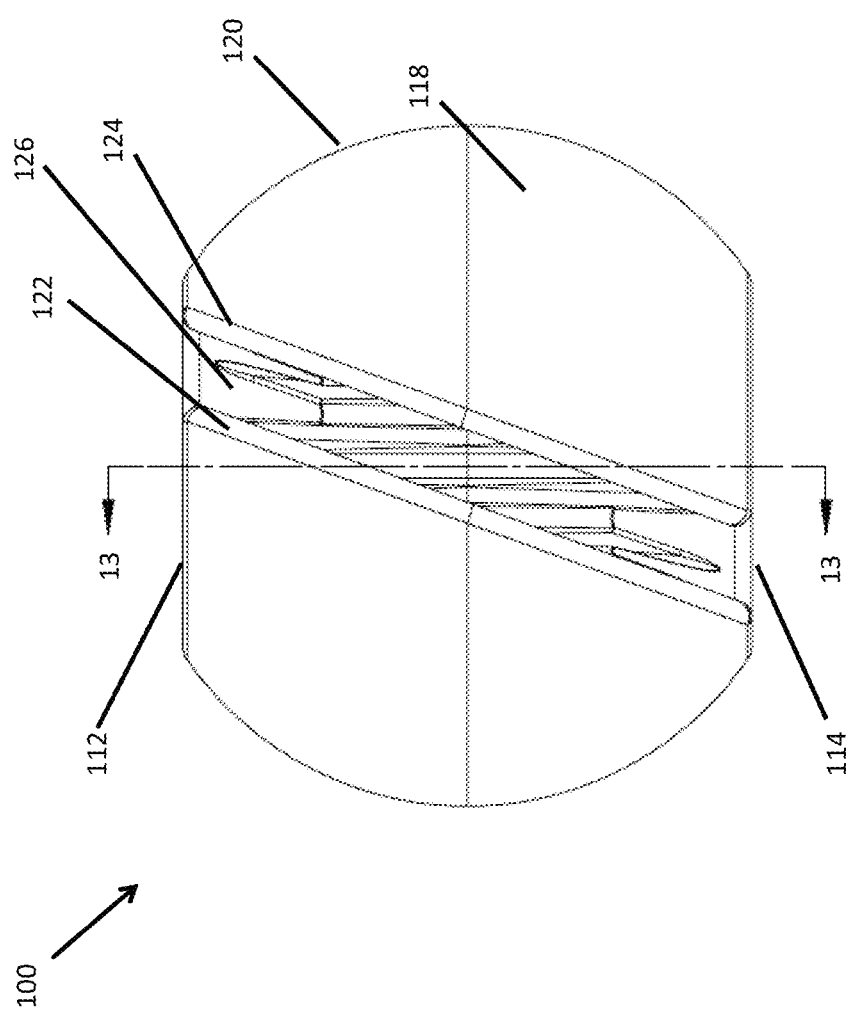
FIG. 12 illustrates a front view of the extremity offloading system of FIGS. 9-11.

The body 110 can have a longitudinal axis extending along the length of the body 120, which can extend between a proximal end and a distal end. As shown in FIG. 12, the body 110 can have an opening 126 that extends through a side of the body 110, such that the opening 126 extends through the thickness of the body 110 on the front or anterior side of the body 110. The opening can extend from the outer surface 118 to the inner surface 130. In this manner, the opening 126 provides access to the central aperture defined by the inner surface 130. In this manner, the outer surface 118 and the inner surface 130 are discontinuous along the circumference of the extremity offloading system 100. The opening 126 can extend from the proximal end 112 to the distal end 114 of the body 110. The opening 126 can be straight, such that it is substantially parallel to the longitudinal axis of the body 110. As illustrated in FIG. 12, the opening 26 can be slanted or angled, such that it is slanted or angled relative to the longitudinal axis of the body 110. In some embodiments, the slant or angle of the opening can be 5 degrees, 10 degrees, 15 degrees, 20 degrees, 25 degrees, 30 degrees, 35 degrees, 40 degrees, or 45 degrees, or any angle in between the foregoing or lesser or greater than the foregoing. The body 110 can have a first edge 122 and a second edge 124 wherein the space between the first edge 122 and the second edge 124 define the first opening 126. The first edge 122 can be considered a medial edge. The second edge 124 can be considered a lateral edge. In some examples, the medial edge and the lateral edge may be reversed. The first edge 122 can be parallel to the second edge 124. The first edge 122 can be separated from the second edge 124 to define the first opening 26. The first edge 112 can be evenly spaced from the second edge 124. In some examples, the first edge 122 and the second edge 124 can each be beveled. The beveled edges can advantageously allow the body 110 to remain secured to the patient. In some examples, the first edge 122 and the second edge 124 can each be straight edges. In some examples, the width of the opening 126 can be between 0.5 inches to 2 inches, such as between 0.5 inches to 1 inch, between 1 to 1.5 inches, between 1.5 inches to 2 inches.

The extremity offloading system 100 can be configured to receive a portion of a leg or ankle of a patient. Similar to extremity offloading system 10 as shown in FIG. 8A, in the open position, the extremity offloading system 100 can be opened to receive the portion of a leg or ankle. In the open position, the first edge 122 and the second edge 124 of the body 110 can be in widened or separated. The first edge 122 and the second edge 124 of the body 110 can be separated to widen or increase the size of first opening 126. The material of the body 110 can be flexible enough to allow the opening 126 to be opened and be resilient enough to close the opening 126 to secure the extremity offloading system 100 to the patient. The opening 126 may automatically close when released by a user, or may be manually closed by the user.

As the patient's leg or ankle is inserted through the opening 126, the patient's leg or ankle may then be inserted in the space or aperture of the extremity offloading system 100. As described above, the space or aperture may be defined by the inner surface 130 of the body 110. The inner surface 130 of the the body 110 can be configured to at least partially wrap around the portion of the patient's leg or ankle. The patient's leg or ankle being inserted to the central space or aperture of the extremity offloading system 100 can cause closure of the extremity offloading system 100. This advantageously allows the extremity offloading system 100 to secure to the patient's leg or ankle without the use of straps or other closure components. Without the use of straps or other closure components, the chances of error in installation or application of the extremity offloading system 100 is reduced, which can increase patient compliance and reduce injuries. The ease of application and securement can be done by one healthcare worker as opposed to some other systems which may require multiple people to apply. This can also reduce the need for a caretaker to continually monitor or adjust the extremity offloading system 100 on the patient.

Furthermore, the gravity or weight of the patient's leg or ankle within the central aperture can not only close the extremity offloading system 100, but the gravity or weight of the patient's leg or ankle can keep the extremity offloading system 100 closed. This advantageously allows the extremity offloading system 100 to be positioned on and retained on a patient's leg or ankle without the use of fasteners or straps, thus making it easier and convenient for the patient and improve patient compliance. The overall spherical shape of the extremity offloading system 100 and curvature of the outer surface 118 advantageously allows for gravity to maintain the device in its proper position.

Additionally, the slanted opening 126 along the length of the extremity offloading system 100 allows for easier application of the device for ease and comfort in application and to prevent inadvertent removal of the extremity offloading system 100.

Similar to the extremity offloading system 10 as shown in FIG. 8B, the extremity offloading system 100 in the closed position can surround a portion of the patient's leg or ankle 60. In some examples, the extremity offloading system 100 can be used in patients at risk for DTPI. In some examples, the extremity offloading system 100 can also be used on an amputated limb or extremity, such as on a leg with a below knee amputation. Once a limb is amputated, a patient often puts excess pressure on the opposite limb, for example in order to shift in bed. This increased pressure on the non-amputated limb can subsequently develop into a DTPI. The extremity offloading system 100 can thus be used on either or both of the amputated limb and non-amputated limb. In the closed position, the first edge 122 and the second edge 124 of the body 110 can be in close proximity or substantially closed. In some examples, the first edge 122 and the second edge 124 can be in contact with one another in the closed position. In some examples, the first edge 122 and the second edge 124 of the body 110 can be minimally separated. For example, the opening 126 can be between 0.5 mm to 2 mm, such as between 0.5 mm to 1 mm, 1 mm to 1.5 mm, or 1.5 mm to 2 mm in the closed position. It should be understood that the dimensions are not limited as such and the opening 126 can be lesser or greater than the disclosed examples. When the extremity offloading system 100 is secured to the patient's leg or ankle and the patient's leg is resting substantially parallel to a surface, the extremity offloading system 100 elevates or suspends the patient's heel, thus reducing the weight applied to the back of a patient's heel.

Furthermore, the round outer surface 28, 118 of the first component 20 or the body 110 allows the patient to turn or rotate their leg or ankle 60, while still keeping the heel suspended. This advantageously allows the patient to move or shift while maintaining the desired function of the extremity offloading system 10, 100. Allowing movement also reduces the risk of an occurrence of DTPI to other parts of the body. Further, allowing movement of the limb can also prevent stagnation, thereby reducing chances of development of deep venous thrombosis or blood clots.

The compact size of the extremity offloading system 10, 100 also allows the extremity offloading system 10, 100 to be easily stored and to be easily transported. The compact size of the extremity offloading system 10, 100 also allows the patient's leg to be moved while wearing the extremity offloading system 10, 100.

Additionally, the extremity offloading system 10, 100 can be maintained and retained on the patient while not or minimally interfering with a patient's ability to walk or move. For example, a patient with the extremity offloading system 10, 100 on their leg or ankle can get up into a sitting position, a standing position, or even walk or shift without removing or adjusting extremity offloading system 10, 100.

Another advantage of extremity offloading system 10, 100 is that the foot or heel of the patient is still accessible. Therefore, the heel or foot can still be treated or monitored without removing or adjusting the extremity offloading system 10, 100.

Yet another advantage of the extremity offloading system 10, 100 is that the assemblies can be used in various settings to position the foot or heel in the desired position, such as in a surgical operating room, for a procedure, or for in an imaging setting (such as x-rays).

Sensors

In some embodiments, the extremity offloading system 10, 100 can include one or more sensors to monitor various parameters. For example, the extremity offloading system 10, 100 can include one or more sensors to monitor movement of the system, such as an accelerometer, a gyroscope, or a magnetometer, which can detect various movement of the patients, such as if the patient has gotten up, if the patient is walking, or if the patient has fallen down. In another example, the extremity offloading system 10, 100 can include one or more sensors to measure orientation of the system, such as an accelerometer, a gyroscope, or a magnetometer, which can detect orientation of the system. The one or more sensors can thereby assist a user or a caretaker in ensuring the system is correctly and remains correctly positioned on the patient's leg or ankle. In another example, the extremity offloading system can also include monitoring one or more of EKG waves (such as QRS waves), blood flow, blood pressure, pressure, temperature, glucose levels, position, or any other parameters. In another configuration, the extremity offloading system can include one or more sensors for monitoring humidity or moisture.

The extremity offloading system 10, 100 can include a circuit 150, which can house several circuit elements. The circuit can be a flexible circuit, which can advantageously curve, such as curving to match the curvature of the body 110. The circuit elements can include one or more of a microcontroller, a memory, a wireless communication element (such as Bluetooth sensor), or one or more sensors. In some examples, the one or more sensors may include a temperature sensor, an accelerometer, and a gyroscope. In other examples, the one or more sensors can include an accelerometer, a gyroscope, a magnetometer, a temperature sensor, a flow sensor, a pressure sensor, a friction sensor, a temperature sensor, an EKG sensor, a blood flow sensor, a blood pressure sensor, a glucose sensor, a position sensor, or an orientation sensor. The circuit 150 can be positioned within the extremity offloading system 10, 100. For example, as shown in FIG. 9, the extremity offloading system 100 can have a cutout or pocket in the body 110 configured to receive the circuit 150. The circuit 150 can be positioned in various places within the extremity offloading system 10, 100. The circuit 150 can be positioned on the sides of the extremity offloading system 10, 100, which advantageously prevents the weight of patient's leg being positioned directly on top of the circuit 150.

In some examples, one or more of the sensors can be configured to be positioned near or be in contact with the patient. For example, the one or more sensors can include a temperature probe which is configured to extend from the main circuit board, the temperature sensor probe can be configured to measure a temperature of the patient. Other types of sensors may also be configured as a probe, such as a pressure sensor probe or a humidity sensor probe. In some examples, the one or more sensor probes that are positioned near or in contact with a patient can be covered and protected with a waterproof, breathable fabric material, such as polytetrafluoroethylene (PTFE), like Teflon.

In some examples, the circuit 150 may be a single board or a single piece. In other examples, the circuit 150 may be modular, such that it is made of several pieces. A modular circuit may include at least one piece that is removable from the at least one other piece of the circuit. The at least one piece can include one or more sensors. In this manner, the at least one piece can be removable from the system, which allows the one or more sensors to be changed or replaced. This advantageously allows for repair or to customize the sensors used in the system.

The circuit 150 can be powered by a power component, such as with a battery. The battery can be rechargeable. The battery can be recharged with a cable, such as with a port through a surface of the extremity offloading system 10, 100. The battery can also be rechargeable through motion or wirelessly.

The circuit 150 can include a wireless communication element, such as a Bluetooth sensor. In some examples, the wireless communication element can include a radio or an antenna or antenna array, which may be configured to communicate on a medical device communications band. The wireless communication element can be configured to wirelessly transmit sensor data from the one or more sensors to a computing device, such as a phone, a tablet, or a computer. In some examples, the data can be received and displayed on the computing device. In other examples, the data can be received by the computing device, which can then perform calculations with the data. The computing device can also process the data to present the data in different visual ways, such as graphically or in a chart.

The use of monitoring various parameters can advantageously allow for remote monitoring methods, especially in consideration to telehealth. In some embodiments, an intermittent compression device can be coupled with the extremity offloading system 10, 100. The use of the intermittent compression device and the extremity offloading system 10, 100 would reduce or prevent the chances of both deep vein thrombosis (DVT) and HAPIs. The intermittent compression device could be positioned on a leg of the patient, such as on the calf of the patient, where the intermittent compression device is proximal to the extremity offloading system 10 in use.

ADDITIONAL EMBODIMENTS

In some embodiments, the extremity offloading system 10, 100 can include a stretchable wrap or band that is positioned around the outer surface of the extremity offloading system. This wrap or band can include elastic strap edging that would provide added security of the extremity offloading system 10, 100 to the patient's leg. The wrap or band could also provide a non-abrasive material against the surface on which the extremity offloading system 10, 100 is positioned on.

In some examples, the extremity offloading system 10, 100 can include a cloth that extends from the first end or the second end of the extremity offloading system. This cloth may be used to secure to the patient's leg or foot. For example, the cloth may be a sock configured to cover a foot and may be used to further secure the extremity offloading system to the patient.

In some examples, the extremity offloading system 10, 100 can include a cloth or stocking that is configured to cover an inner surface 50, 130. The cloth can be configured to be positioned between the inner surface 50, 130 and the skin of a patient. This cloth can be used to prevent skin irritation of a patient and prevent slippage of the system from the patient.

In some examples, the cloth or stocking attached to an inner surface or extending from the first end or the second end can include the one or more sensors or circuit 150 as previously described herein.

CONCLUSION

Embodiments of systems, components and methods of assembly and manufacture are described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "proximal," "distal," "lateral," "medial," "anterior," "posterior," "top," "bottom," "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import. The use of any of the terms are not intended to limit the directionality or orientation of the device.

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. An extremity offloading system comprising:
a body comprising an outer surface, an inner surface, and a thickness extending between the outer surface and the inner surface, the outer surface being substantially spherical, the inner surface defining an aperture;
wherein the aperture is configured to accept insertion of a leg or an ankle of a patient.

2. The extremity offloading system of claim 1, wherein the body comprises a proximal end and a distal end, wherein the aperture extends through the proximal end and the distal.

3. The extremity offloading system of claim 2, wherein the proximal end and the distal end are each flat.

4. The extremity offloading system of claim 1, wherein the aperture is cylindrical.

5. The extremity offloading system of claim 4, wherein a diameter of the aperture at the proximal end and a diameter of the aperture at the distal end are each greater than a diameter of the aperture at the middle of the body.

6. The extremity offloading system of claim 1, wherein the inner surface comprises a plurality of flutes.

7. The extremity offloading system of claim 6, wherein a length of each of the plurality of flutes extend along a length of the aperture.

8. The extremity offloading system of claim 6, wherein each of the plurality of flutes are equally spaced about a circumference of the aperture.

9. The extremity offloading system of claim 6, wherein the plurality of flutes comprises 10 flutes.

10. The extremity offloading system of claim 6, wherein the inner surface comprises a plurality of portions between each of the plurality of flutes.

11. The extremity offloading system of claim 10, wherein each of the plurality of portions comprises a flat surface, each flat surface configured to be in contact with the leg or the ankle of the patient.

12. The extremity offloading system of claim 10, wherein corners between each of the plurality of flutes and each of the plurality of portions are rounded.

13. The extremity offloading system of claim 1, wherein the body comprises an opening extending through a side of the body, wherein the opening extends through the thickness of the body between the outer surface and the inner surface.

14. The extremity offloading system of claim 1, further comprising one or more sensors configured to measure one or more of movement, pressure, temperature, humidity, or at least one patient parameter.

15. The extremity offloading system of claim 14, wherein the one or more sensors comprises at least an accelerometer, a gyroscope, and a temperature sensor.

16. The extremity offloading system of claim 1, wherein the body comprises foam.

17. An extremity offloading system comprising:
a body comprising an outer surface, an inner surface, and a thickness extending between the outer surface and the inner surface, the outer surface being at least partially round, the inner surface defining an aperture;

wherein the aperture is configured to accept insertion of a leg or an ankle of a patient, wherein the body comprises an opening extending through a side of the body, wherein the opening extends through the thickness of the body between the outer surf ace and the inner surface and the opening has a length that extends along a length of the body, wherein the opening length of the opening is angled at least 5 degrees relative to a longitudinal axis of the body, the longitudinal axis extending from a proximal end to a distal end of the body.

18. The extremity offloading system of claim 17, wherein the opening is defined by a first edge and a second edge of the body.

19. The extremity offloading system of claim 18, wherein the first edge and the second edge are parallel.

20. The extremity offloading system of claim 18, wherein the first edge and the second edge are each beveled.

* * * * *

UNITED STATES PATENT AND TRADEMARK OFFICE
CERTIFICATE OF CORRECTION

PATENT NO. : 11,877,960 B2  
APPLICATION NO. : 17/455342  
DATED : January 23, 2024  
INVENTOR(S) : Michael J. Marcus Page 1 of 1

It is certified that error appears in the above-identified patent and that said Letters Patent is hereby corrected as shown below:

In the Specification

In Column 1, Line 66, delete "distal." and insert --distal end.--.

In Column 3, Line 49, delete "DPTIs," and insert --DTPIs,--.

In Column 12, Line 65, delete "the the" and insert --the--.

In the Claims

In Column 18, Claim 2, Line 21, delete "distal." and insert --distal end.--.

In Column 19, Claim 17, Line 6, delete "surf ace" and insert --surface--.

In Column 19, Claim 17, Line 9, before "length", delete "opening".

Signed and Sealed this  
Twenty-third Day of April, 2024

Katherine Kelly Vidal  
*Director of the United States Patent and Trademark Office*